(12) United States Patent
Kasahara et al.

(10) Patent No.: US 9,158,196 B2
(45) Date of Patent: Oct. 13, 2015

(54) RADIATION-SENSITIVE RESIN COMPOSITION AND PATTERN-FORMING METHOD

(71) Applicant: JSR CORPORATION, Tokyo (JP)

(72) Inventors: Kazuki Kasahara, Tokyo (JP); Hiromitsu Nakashima, Tokyo (JP); Masafumi Hori, Tokyo (JP); Masafumi Yoshida, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 13/851,158

(22) Filed: Mar. 27, 2013

(65) Prior Publication Data

US 2013/0216948 A1  Aug. 22, 2013

Related U.S. Application Data

(63) Continuation of application No. PCT/JP2011/072297, filed on Sep. 28, 2011.

(30) Foreign Application Priority Data

Sep. 29, 2010 (JP) ................................. 2010-220071

(51) Int. Cl.
| | |
|---|---|
| *G03F 7/004* | (2006.01) |
| *G03F 7/20* | (2006.01) |
| *C08F 220/20* | (2006.01) |
| *H01L 21/027* | (2006.01) |
| *C07D 307/93* | (2006.01) |
| *C07D 493/18* | (2006.01) |
| *G03F 7/039* | (2006.01) |
| *G03F 7/38* | (2006.01) |

(52) U.S. Cl.
CPC .............. *G03F 7/004* (2013.01); *C07D 307/93* (2013.01); *C07D 493/18* (2013.01); *C08F 220/20* (2013.01); *G03F 7/039* (2013.01); *G03F 7/0397* (2013.01); *G03F 7/2041* (2013.01); *G03F 7/38* (2013.01); *H01L 21/0274* (2013.01); *H01L 21/0275* (2013.01)

(58) Field of Classification Search
CPC ..... G03F 7/004; G03F 7/0397; G03F 7/0045; G03F 7/38; G03F 7/2041; C08F 222/20; C07D 307/93; C07D 493/18; H01L 21/027; H01L 21/0271; H01L 21/0273; H01L 21/0274; H01L 21/0275
USPC ............... 430/270.1, 913, 330, 331, 322, 905
See application file for complete search history.

(56) References Cited

U.S. PATENT DOCUMENTS

| | | | |
|---|---|---|---|
| 6,388,101 B1 | 5/2002 | Hada et al. | |
| 8,039,197 B2 * | 10/2011 | Kanda et al. | 430/270.1 |
| 8,415,082 B2 * | 4/2013 | Utsumi et al. | 430/270.1 |
| 2008/0026331 A1 * | 1/2008 | Hasegawa et al. | 430/327 |
| 2008/0193874 A1 * | 8/2008 | Takata et al. | 430/270.1 |
| 2009/0068588 A1 * | 3/2009 | Kinoshita et al. | 430/285.1 |
| 2009/0233242 A1 * | 9/2009 | Hasegawa et al. | 430/325 |

(Continued)

FOREIGN PATENT DOCUMENTS

| | | |
|---|---|---|
| JP | 09-73173 | 3/1997 |
| JP | 09-90637 | 4/1997 |

(Continued)

OTHER PUBLICATIONS

International Search Report for corresponding International Application No. PCT/JP2011/072297, Oct. 25, 2011.

(Continued)

*Primary Examiner* — Amanda C Walke
(74) *Attorney, Agent, or Firm* — Oblon, McClelland, Maier & Neustadt, L.L.P.

(57) ABSTRACT

A radiation-sensitive resin composition for forming a resist film includes a polymer including a first structural unit represented by a formula (1) and a second structural unit represented by a formula (2). The first structural unit and the second structural unit are included in an identical polymer molecule or different polymer molecules. $R^1$ represents a hydrogen atom or a methyl group. Q represents a divalent linking group having 1 to 4 carbon atoms. X represents a monovalent lactone group. A part or all of hydrogen atoms included in the monovalent lactone group represented by X are not substituted or substituted. $R^2$ represents a hydrogen atom or a methyl group. Y represents a monovalent lactone group. A part or all of hydrogen atoms included in the monovalent lactone group represented by Y are not substituted or substituted.

(1)

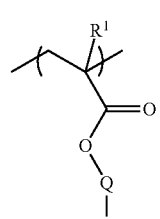

(2)

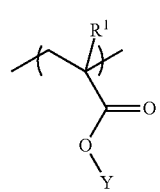

12 Claims, No Drawings

(56) References Cited

U.S. PATENT DOCUMENTS

| | | | |
|---|---|---|---|
| 2009/0274984 A1* | 11/2009 | Shinachi et al. | 430/325 |
| 2011/0269072 A1* | 11/2011 | Shibuya | 430/270.1 |

FOREIGN PATENT DOCUMENTS

| | | |
|---|---|---|
| JP | 10-274852 | 10/1998 |
| JP | 2000-26446 | 1/2000 |
| JP | 2000-122294 | 4/2000 |
| JP | 2000-159758 | 6/2000 |
| JP | 2001-109154 | 4/2001 |
| JP | 2002-308866 | 10/2002 |
| JP | 2002-371114 | 12/2002 |
| JP | 2003-64134 | 3/2003 |
| JP | 2003-113174 | 4/2003 |
| JP | 2003-147023 | 5/2003 |
| JP | 2003-270787 | 9/2003 |
| JP | 2004-101642 | 4/2004 |
| JP | 2004-210917 | 7/2004 |
| JP | 2005-248153 | 9/2005 |
| JP | 2006-227632 | 8/2006 |
| JP | 2008-031298 | 2/2008 |
| JP | 2008-170983 | 7/2008 |
| JP | 2008-209917 | 9/2008 |
| JP | 2010-033032 | 2/2010 |
| JP | 2010-186176 | 8/2010 |
| JP | 2010-224066 | 10/2010 |
| JP | 2010-224522 | 10/2010 |
| JP | 2011-191731 | 9/2011 |
| TW | 200815484 A | 4/2008 |
| TW | 201007357 A1 | 2/2010 |
| WO | WO 2005/069076 | 7/2005 |
| WO | WO 2006/035790 | 4/2006 |
| WO | WO 2010/061875 | 6/2010 |

OTHER PUBLICATIONS

Office Action issued Nov. 4, 2014, in Japanese Patent Application No. 2012-536529 (w/ English-language Translation).

Office Action issued Mar. 23, 2015, in Taiwan Patent Application No. 100135227 filed Sep. 29, 2011 (w/English translation).

* cited by examiner

RADIATION-SENSITIVE RESIN COMPOSITION AND PATTERN-FORMING METHOD

CROSS-REFERENCE TO RELATED APPLICATIONS

The present application is a continuation application of International Application No. PCT/JP2011/072297, filed Sep. 28, 2011, which claims priority to Japanese Patent Application No. 2010-220071, filed Sep. 29, 2010. The contents of these applications are incorporated herein by reference in their entirety.

BACKGROUND OF THE INVENTION

The present invention relates to a radiation-sensitive resin composition and a pattern-forming method.

FIELD OF THE INVENTION

In the field of microfabrication represented by manufacturing of integrated circuit elements and the like, in order to obtain higher integrity, lithography techniques using radioactive rays with shorter wavelengths typified by a KrF excimer laser (wavelength: 248 nm), an ArF excimer laser (wavelength: 193 nm) and the like have been developed. As resist films for use with the above-mentioned excimer laser, chemically amplified resist films are typically used which contain a component having an acid-dissociable group, and an acid generating agent generating an acid upon irradiation with radioactive rays. In such chemically amplified resist films, patterns can be formed by generating the acid in light-exposed sites by irradiation with the radioactive rays, allowing chemical reactions catalyzed by the acid to occur, and the difference in dissolution rate in a developer solution between the light-exposed sites and light-unexposed sites to be caused. A large number of radiation-sensitive resin compositions useful for the chemically amplified resist film material have been proposed.

For example, as a radiation-sensitive resin composition which responses to the ArF excimer laser, a radiation-sensitive resin composition is known which contains a lactone-containing (meth)acrylic polymer in view of achieving superior resolving ability and depth of focus (see, Japanese Unexamined Patent Application, Publication No. H9-90637, Japanese Unexamined Patent Application, Publication No. H10-274852, and Japanese Unexamined Patent Application, Publication No. 2000-26446). Specific examples thereof include a radiation-sensitive resin composition containing a polymer having a mevalonic lactone skeleton and/or a γ-butyrolactone skeleton as a constitutional component (see, Japanese Unexamined Patent Application, Publication No. H9-73173 and U.S. Pat. No. 6,388,101), a radiation-sensitive resin composition containing a polymer having an alicyclic lactone skeleton in its structural unit as a constitutional component (see, Japanese Unexamined Patent Application, Publication No. 2000-159758, Japanese Unexamined Patent Application, Publication No. 2001-109154, Japanese Unexamined Patent Application, Publication No. 2004-101642, Japanese Unexamined Patent Application, Publication No. 2003-113174, Japanese Unexamined Patent Application, Publication No. 2003-147023, Japanese Unexamined Patent Application, Publication No. 2002-308866, Japanese Unexamined Patent Application, Publication No. 2002-371114, Japanese Unexamined Patent Application, Publication No. 2003-64134, Japanese Unexamined Patent Application, Publication No. 2003-270787, and Japanese Unexamined Patent Application, Publication No. 2000-122294), and the like.

However, in recent years when further microfabrication of devices in progress, resist films are required which are superior in sensitivity, which is a basic property, and the like and have highly balanced performance of MEEF (Mask Error Enhancement Factor), which is a measure of a mask error latitude, DOF (depth of focus), LWR (Line Width Roughness), CDU (Critical Dimension Uniformity) and the like. In addition, a disadvantage has been pointed out in regard to the use of conventional radiation-sensitive resin compositions that when a heating temperature in pattern formation is comparatively high, the resolution of the compositions is impaired.

SUMMARY OF THE INVENTION

According to one aspect of the present invention, a radiation-sensitive resin composition for forming a resist film includes a polymer including a first structural unit represented by a formula (1) and a second structural unit represented by a formula (2). The first structural unit and the second structural unit are included in an identical polymer molecule or different polymer molecules.

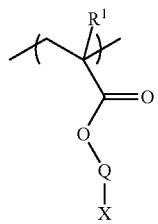

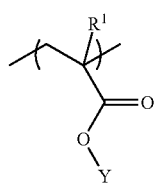

In the formula (1), $R^1$ represents a hydrogen atom or a methyl group. Q represents a divalent linking group having 1 to 4 carbon atoms. X represents a monovalent lactone group. A part or all of hydrogen atoms included in the monovalent lactone group represented by X are not substituted or substituted. In the formula (2), $R^2$ represents a hydrogen atom or a methyl group. Y represents a monovalent lactone group. A part or all of hydrogen atoms included in the monovalent lactone group represented by Y are not substituted or substituted. The radiation-sensitive resin composition is for use in a pattern-forming method. The method includes providing the resist film on a substrate, exposing the resist film, heating the exposed resist film at a temperature of no greater than 110° C., and developing the heated resist film.

According to another aspect of the present invention, a pattern-forming method includes coating the radiation-sensitive resin composition on a substrate to provide a resist film, exposing the resist film, heating the exposed resist film at a temperature of no greater than 110° C., and developing the heated resist film.

DESCRIPTION OF THE EMBODIMENTS

An embodiment of the invention, which has been made for solving the foregoing problems, relates to a radiation-sensitive resin composition for forming a resist film for use in a pattern-forming method, the pattern-forming method includes the steps of:

(1) providing a resist film on a substrate;
(2) exposing the resist film;
(3) heating the exposed resist film at a temperature of no greater than 110° C.; and
(4) developing the heated resist film, the radiation-sensitive resin composition containing (A) a polymer having, in an identical polymer molecule or different polymer molecules, a structural unit (I) represented by the following formula (1) and a structural unit (II) represented by the following formula (2):

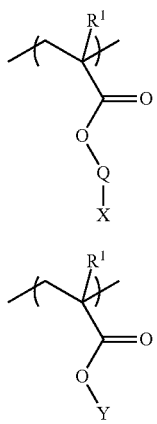

wherein, in the formula (1), $R^1$ represents a hydrogen atom or a methyl group; Q represents a divalent linking group having 1 to 4 carbon atoms; and X represents a monovalent lactone group, wherein a part or all of hydrogen atoms included in the monovalent lactone group are not substituted or substituted; and in the formula (2), $R^2$ represents a hydrogen atom or a methyl group; and Y represents a monovalent lactone group, wherein a part or all of hydrogen atoms included in the monovalent lactone group are not substituted or substituted.

When the radiation-sensitive resin composition is used in the pattern-forming method, the resist film provided is superior in sensitivity, which is a basic property of resists, further has highly-balanced LWR, DOF, MEEF, CDU and the like, and superior in lithography property. Without wishing to be bound to particular reasons for the above-mentioned effect to be exerted by the radiation-sensitive resin composition, for example, the following may be assumed. The radiation-sensitive resin composition contains the polymer (A) having, in an identical polymer molecule or different polymer molecules, the structural unit (I) represented by the above formula (1) and the structural unit (II) represented by the above formula (2). The structural unit (I) has a group represented by the Q between the monovalent lactone group and the ester group. On the other hand, the structural unit (II) has an ester group directly bonded to the monovalent lactone group. When the polymer (A) has both of the structural units, the lactone group moieties from the both structural units tend to be dispersedly located around the periphery of the polymer chain, spaces are secured, and rigidity of the polymer is moderately reduced. This results in easier penetration of a developer solution into the polymer (A), which increases the solubility of the polymer (A) in the developer solution. Moreover, for the same reason described above, a reaction, for example, of an acid generated form an acid generating agent and the like with an acid-dissociable group, and the like is also promoted. As a result of these effects, the resist film provided by the radiation-sensitive resin composition has highly-balanced LWR, DOF, MEEF, CDU and the like, and is superior in lithography property. Moreover, when the radiation-sensitive resin composition is employed, the temperature of the post exposure baking (PEB) may be set to no greater than 110° C., whereby energy consumption in the manufacturing process thereof may be saved.

It is preferred that all the hydrogen atoms included in the lactone groups represented by X and Y are not substituted. The absence of any substituent in the monovalent lactone groups included in the structural unit (I) and the structural unit (II) leads to improvement of adhesiveness and lithography property such as the LWR of the resist film provided by the radiation-sensitive resin composition.

The Q is preferably —$CH_2CH_2O$—* or —$CH_2COO$—*, wherein * indicates a bonding site to the group represented by X. In the structural unit represented by the above formula (1), when Q is the linking group of the specific structure, more favorable distribution of the lactone groups around the polymer chain is achieved, and thereby the lithography properties of the resultant resist film such as the LWR tend to be improved.

It is preferred that the groups represented by the X and Y are identical. When the lactone skeleton-bearing groups included in the structural unit (I) and the structural unit (II) are groups of an identical structure, solubility of the polymer (A) becomes higher and thereby the lithography property of the resultant resist film such as the LWR tend to be further improved. In addition, when the groups represented by the X and Y are identical, synthesis of the polymer (A) is convenient.

It is preferred that the lactone groups represented by the X and Y have a norbornane lactone skeleton. When the lactone groups included in the structural unit (I) and the structural unit (II) have the norbornane lactone skeleton, the lithography property of the resultant resist film such as the LWR, and adhesiveness to a substrate and the like are tend to be simultaneously achieved at a higher level.

The Mw/Mn of the polymer (A) is preferably no less than 1.0 and no greater than 1.5. When the Mw/Mn of the polymer (A) is in the above-specified range, the resist film provided by the radiation-sensitive resin composition is likely to be superior in resolving performance.

The embodiment of the present invention encompasses a pattern-forming method, including the steps of:

(1) coating the radiation-sensitive resin composition according to the embodiment of the present invention onto a substrate to provide a resist film;
(2) exposing the resist film;
(3) heating the exposed resist film at a temperature of no greater than 110° C.; and
(4) developing the heated resist film.

The pattern-forming method according to the embodiment of the present invention allows for the formation of a fine pattern exhibiting superior LWR and the like.

It should be noted that the "radiation" in the "radiation-sensitive resin composition" as referred to herein includes visible light rays, ultraviolet rays, far ultraviolet rays, X-rays, charged particle rays, and the like.

According to the embodiment of the present invention, there can be provided a radiation-sensitive resin composition capable of forming a resist film which is superior in not only basic properties such as sensitivity, but also lithography properties such as LWR, MEEF, DOF and CDU, and which can form a favorable fine pattern even at comparatively low heating temperatures in a heating step of a resist pattern-forming method. The embodiments will now be described in detail.

Radiation-Sensitive Resin Composition

The radiation-sensitive resin composition according to an embodiment of the present invention contains a polymer (A). In addition, the radiation-sensitive resin composition may contain (B) a fluorine atom-containing polymer, (C) an acid generator, (D) an acid diffusion controller, and (E) a solvent as required, and may further contain other optional components as long as the effects of the present invention are not impaired. Hereinafter, the each component will be explained in detail.

Polymer (A)

The polymer (A) included in the radiation-sensitive resin composition has, in an identical polymer molecule or different polymer molecules, a structural unit (I) represented by the above formula (1) and a structural unit (II) represented by the above formula (2).

The embodiments of the polymer (A) having the structural unit (I) and the structural unit (II) is not particularly limited, and include the following: (i) the case where one kind of polymer molecule is included in the polymer (A), and the one kind of polymer molecule has both of the structural unit (I) and the structural unit (II), (ii) the case where two kinds of polymer molecules are included in the polymer (A), and one of the two kinds of polymer molecules has the structural unit (I) while the other of the two kinds of polymer molecules has the structural unit (II), (iii) the case where three kinds of polymer molecules are included in the polymer (A), and one of the three kinds of polymer molecules has both of the structural unit (I) and the structural unit (II), another of the three kinds of polymer molecules has the structural unit (I), and yet another of the three kinds of polymer molecules has the structural unit (II), and (iv) the case where, in addition to the polymer molecules defined in (i) to (iii), another one or two or more kinds of polymer molecules are included in the polymer (A), and the like. In any case, the effects of the present invention can be enjoyed.

The structural unit (I) has a group represented by the Q between the monovalent lactone group and an ester group, whereas the structural unit (II) has a monovalent lactone group directly bonded to an ester group. When the polymer (A) includes both of the structural units, the lactone group moieties from the both structural units tend to be dispersedly located around the polymer chain, certain spaces are reserved, and rigidity of the polymer tend to be moderately reduced. As a result, affinity between the polymer (A) and a developer solution is enhanced, and hence solubility of the polymer (A) in a developer solution is increased. For the same reasons as those mentioned above, the reaction of an acid generated from an acid generating agent and the like with an acid-dissociable group, and the like, is also promoted. As a result of these effects, resolving ability of the resulting pattern is considered to be improved.

The polymer (A) has, in an identical polymer molecule or different polymer molecules, the structural unit (I) and the structural unit (II) as described above, and further has a structural unit (III) including an acid-dissociable group represented by the following formula (4), and a structural unit (IV) including a hydroxyl group, as required. Hereinafter, each structural unit will be explained in detail.

Structural Unit (I)

In the formula (1), $R^1$ represents a hydrogen atom or a methyl group. Q represents a divalent linking group having 1 to 4 carbon atoms. X represents a monovalent lactone group, wherein a part or all of hydrogen atoms included in the monovalent lactone group are not substituted or substituted.

In the above formula (1), the divalent linking group having 1 to 4 carbon atoms represented by the Q is preferably a group represented by the following formula (3):

wherein, in the formula (3), $R^3$ represents an alkylene group having 1 to 3 carbon atoms; and $R^4$ represents a single bond or a carbonyl group, wherein * indicates a bonding site to the X in the formula (1).

In the above formula (3), examples of the alkylene group having 1 to 3 carbon atoms represented by $R^3$ include a methylene group, an ethylene group, and a propylene group. Among these, the methylene group and the ethylene group are preferred, and Q is preferably —$CH_2CH_2O$—* and —$CH_2COO$—*.

In the above formula (1), the X represents a monovalent lactone group. Used herein, the lactone group stands for a group obtained by removing one hydrogen atom from a lactone ring. In addition, the lactone ring stands for a single cycle including a bond represented by —O—C(O)—. The lactone ring is counted as a first ring; when the lactone ring alone is present, the lactone group is referred to as a monocyclic formula group; and when the lactone group additionally includes other ring structures, the lactone group is referred to as a polycyclic group, irrespective of the structure included therein.

Examples of the monovalent lactone group represented by the X include groups represented by the following formulae (L-1) to (L-6), and the like:

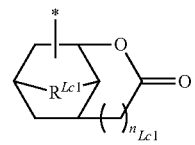

(L-1)

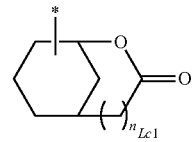

(L-2)

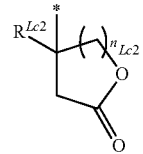

(L-3)

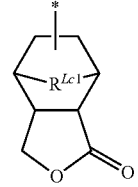

(L-4)

(L-5)

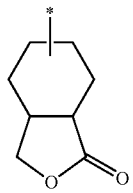

(L-6)

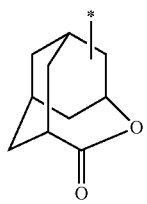

wherein, in the formulae (L-1) to (L-6), $R^{Lc1}$ represents an oxygen atom or a methylene group; $R^{Lc2}$ represents a hydrogen atom or an alkyl group having 1 to 4 carbon atoms; $n_{Lc1}$ is 0 or 1; $n_{Lc2}$ is an integer of 0 to 3; * indicates a bonding site to the Q in the formula (1); and furthermore, the groups represented by formulae (L-1) to (L-6) may have a substituent.

Examples of the substituent that is optionally included in the monovalent lactone group include a linear or branched alkyl group having 1 to 4 carbon atoms, a linear or branched alkoxy group having 1 to 4 carbon atoms, and the like. Of these, the methyl group or the ethyl group is preferred.

In addition, in some preferred embodiments, the monovalent lactone group may include a monovalent lactone group having a substituent other than a cyano group. When the lactone group has a substituent other than the cyano group, lithography performance such as the LWR tends to be improved.

Furthermore, in other preferred embodiments, the monovalent lactone group may include a monovalent lactone group having no substituent. When the lactone group has no substituent, the lithography performance such as the LWR tends to be improved while improving the adhesiveness of the resultant resist film.

Examples of the structural unit (I) include structural units represented by the following formulae, and the like:

(1-1)

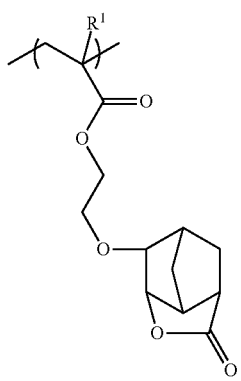

(1-2)

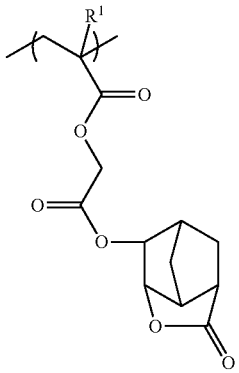

(1-3)

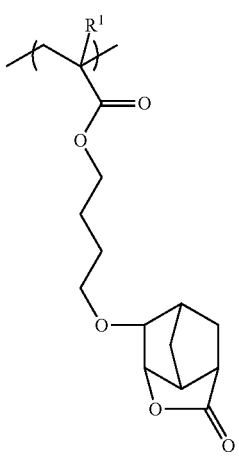

wherein, in the formulae, $R^1$ is as defined in the above formula (1).

Among these, the structural units represented by the formulae (1-1) and (1-2) are preferred.

The content of the structural unit (I) in the polymer (A) is such that the total amount of the structural unit (I) is preferably 2 mol % to 70 mol %, and more preferably 5 mol % to 40 mol % with respect to entire structural units constituting the polymer (A). In addition, the polymer (A) may have one, or two or more types of the structural unit (I).

Structural Unit (II)

In the formula (2), $R^2$ represents a hydrogen atom or a methyl group. Y represents a monovalent lactone group, wherein a part or all of hydrogen atoms included in the lactone group are not substituted or substituted.

In the above formula (2), examples of the monovalent lactone group represented by Y includes the same groups as those exemplified in the above formula (1) as the monovalent lactone group represented by X, and the like.

Examples of the structural unit (II) include structural units represented by the following formulae, and the like:

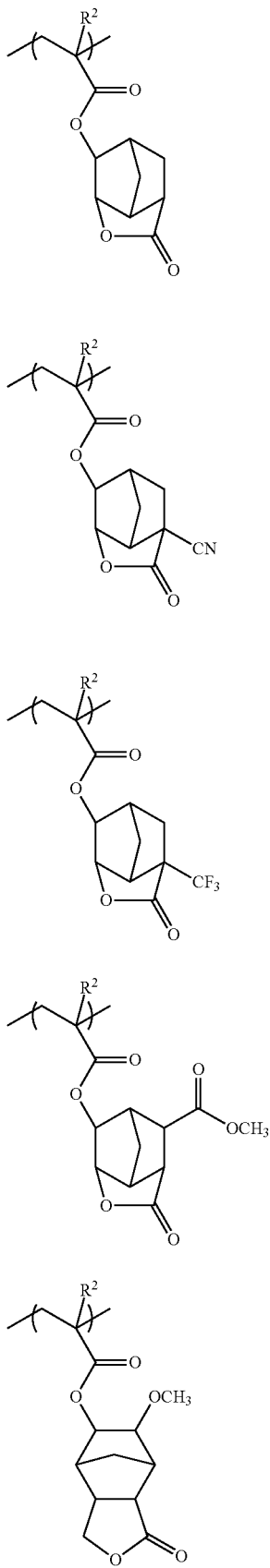
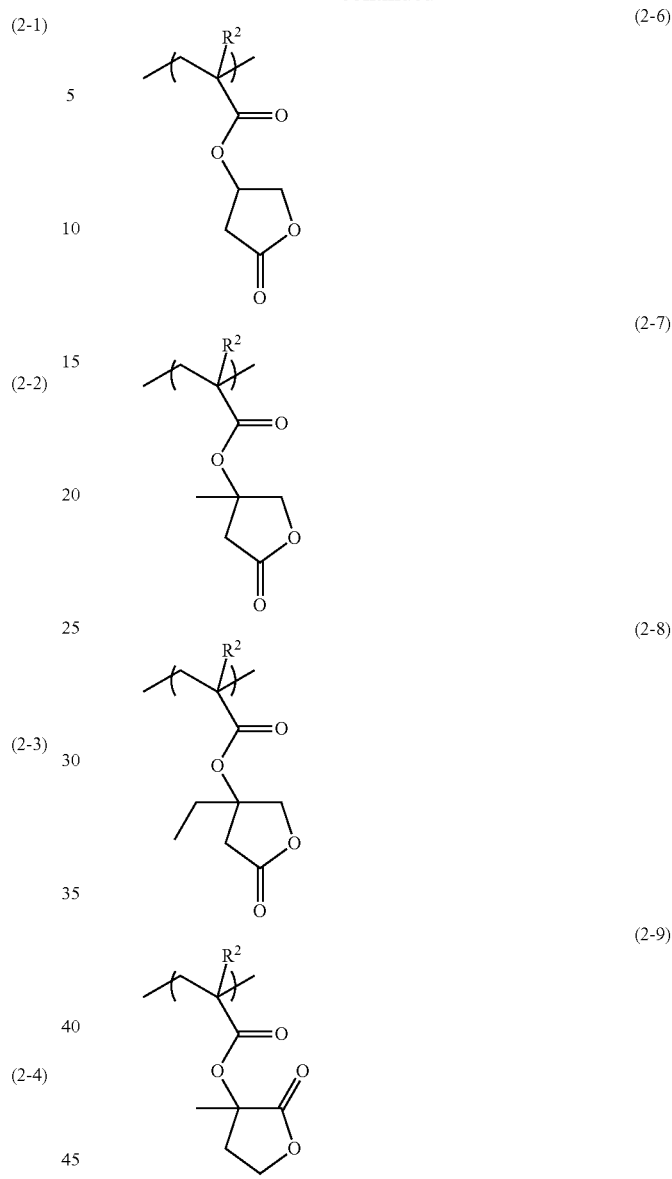

wherein, in the formulae, $R^2$ is as defined in the above formula (2).

Among these, the structural unit represented by the formula (2-1) is preferred.

The content of the structural unit (II) in the polymer (A) is such that the total amount of the structural unit (II) is preferably 5 mol % to 80 mol %, and more preferably 20 mol % to 70 mol % with respect to entire structural units constituting the polymer (A). In addition, the polymer (A) may have one, or two or more types of the structural unit (II).

The polymer (A) has the structural unit (I) and the structural unit (II), and preferably, the lactone groups included in the respective structural units are identical. When the lactone group included in the structural unit (I) and the lactone group included in the structural unit (II) have the identical structure, the LWR of the resultant resist film, and the like tends to be further improved.

Structural Unit (III)

The polymer (A) preferably includes a structural unit (III) including an acid-dissociable group represented by the following formula (4). The acid-dissociable group dissociates via the catalytic action of the acid generated from the acid generator (C) upon exposure. As a result, polarity of the light-exposed sites of the polymer (A) is increased, which causes the difference in dissolution rate in a developer solution between the light-exposed sites and light-unexposed sites, and allows for the formation of a resist pattern exhibiting superior lithography property.

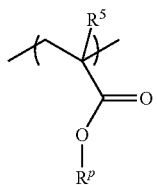

(4)

In the formula (4), $R^5$ represents a hydrogen atom, a methyl group or a trifluoromethyl group. $R^p$ represents an acid-dissociable group.

The acid-dissociable group represented by the $R^p$ is preferably a group represented by the following formula (5):

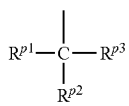

(5)

wherein, in the formula (5), $R^{p1}$ represents an alkyl group having 1 to 4 carbon atoms or a monovalent alicyclic hydrocarbon group having 4 to 20 carbon atoms; $R^{p2}$ and $R^{p3}$ represent, each independently, an alkyl group having 1 to 4 carbon atoms or an alicyclic hydrocarbon group having 4 to 20 carbon atoms; and wherein $R^{p2}$ and $R^{p3}$ may be combined with the carbon atom to which they are bound to form a divalent alicyclic hydrocarbon group having 4 to 20 carbon atoms.

Examples of the alkyl group having 1 to 4 carbon atoms represented by the $R^{p1}$, $R^{p2}$ and $R^{p3}$ include a methyl group, an ethyl group, a n-propyl group, an i-propyl group, a n-butyl group, a 2-methylpropyl group, a 1-methylpropyl group, a t-butyl group, and the like.

Examples of the monovalent alicyclic hydrocarbon group having 4 to 20 carbon atoms represented by the $R^{p1}$, $R^{p2}$ and $R^{p3}$ include:

polycyclic alicyclic groups having a bridged skeleton such as an adamantane skeleton, and a norbornane skeleton;

monocyclic alicyclic groups having a cycloalkane skeleton such as cyclopentane, cyclohexane, and the like. In addition, these groups are not substituted or substituted by, for example, one or more kinds of linear, branched or cyclic alkyl groups having 1 to 10 carbon atoms.

Among these, $R^{p1}$ is preferably the alkyl group having 1 to 4 carbon atoms, and $R^{p2}$ and $R^{p3}$ are preferably combined with the carbon atom to which they are bound to form a divalent group having an adamantane skeleton or a cycloalkane skeleton.

Examples of the structural unit (III) include structural units represented by the following formulae (3-1) to (3-4):

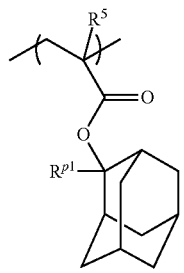

(3-1)

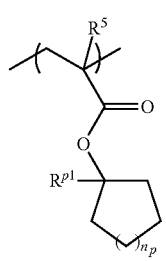

(3-2)

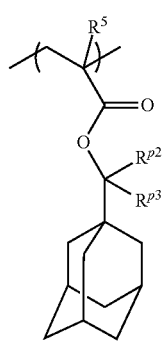

(3-3)

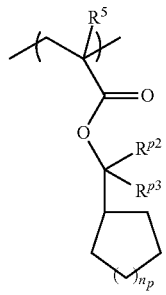

(3-4)

wherein, in the formulae (3-1) to (3-4), $R^5$ is as defined in the above formula (4); $R^{p1}$, $R^{p2}$ and $R^{p3}$ are as defined in the above formula (5); and $n_p$ is an integer of 1 to 3.

Examples of the structural unit represented by the above formula (4) include structural units represented by the following formulae, and the like:

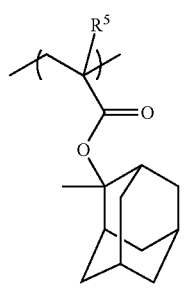 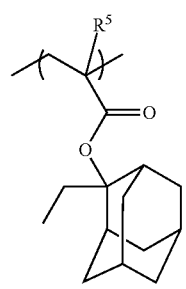

-continued

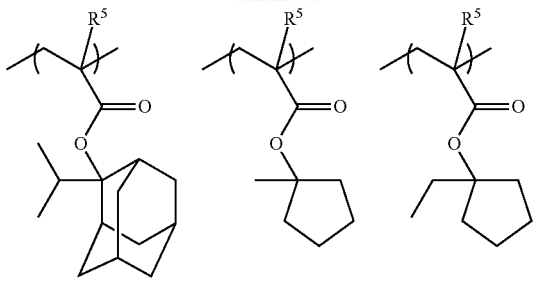
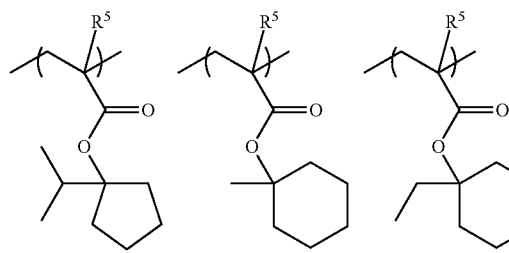
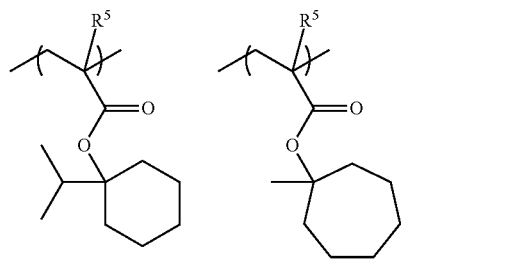
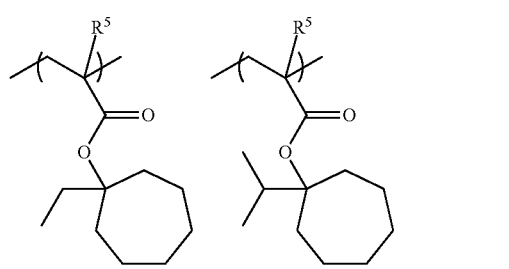
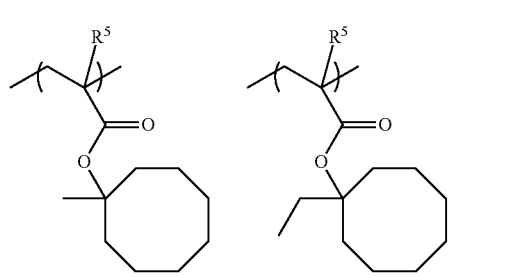
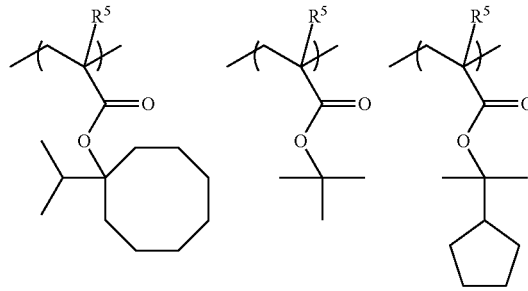

-continued

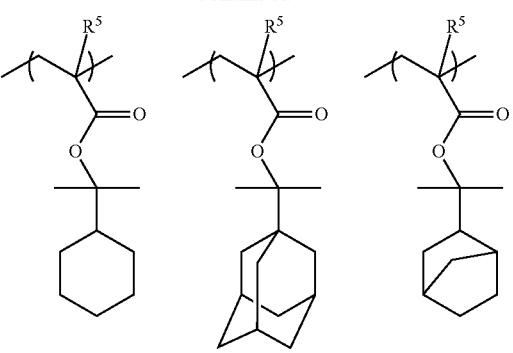

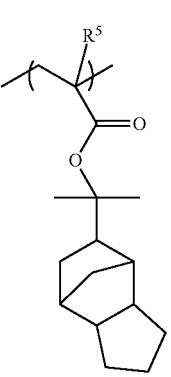

wherein, in the formulae, $R^5$ is as defined in the above formula (4).

The content of the structural unit (III) in the polymer (A) is preferably 20 mol % to 60 mol % with respect to entire structural units constituting the polymer (A). In addition, polymer (A) may have one, or two or more types of the structural unit (III).

Structural Unit (IV)

The polymer (A) may further include a structural unit (IV) including a hydroxyl group represented by the following formulae, and the like, as long as the effects of the present invention are not impaired. The structural unit (IV) is not particularly limited, as long as the structural unit has a hydroxyl group. The number of hydroxyl groups in the structural unit may be 1, or 2 or more. In addition, the position of the hydroxyl group(s) in the structural unit is also not particularly limited. Examples of the structural unit (IV) include structural units represented by the following formulae, and the like:

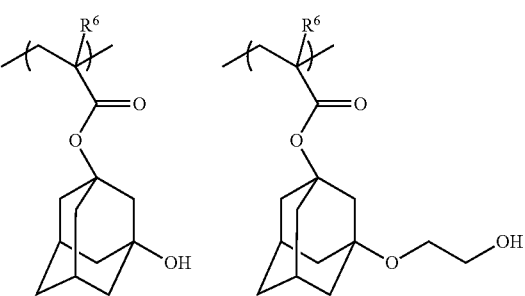

-continued

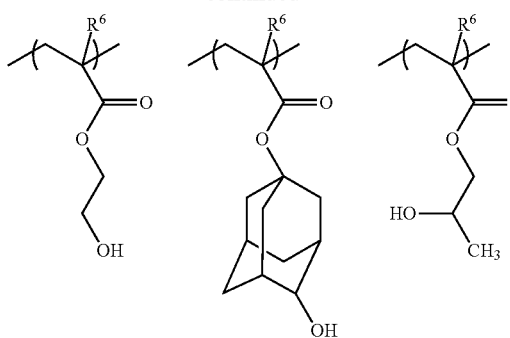
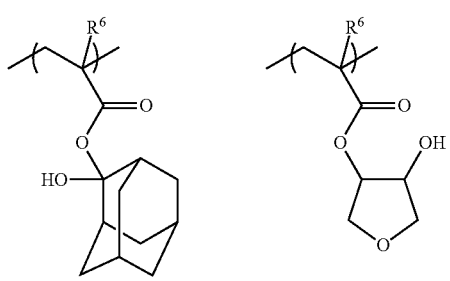
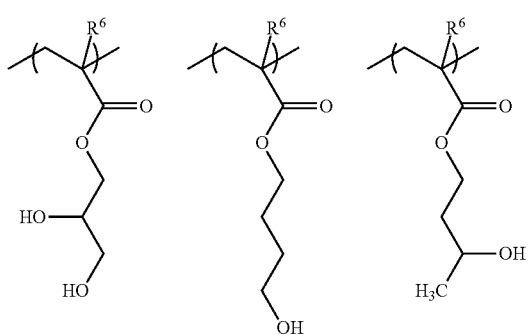
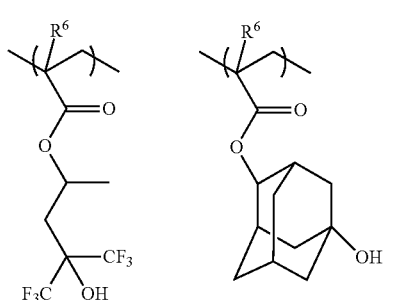
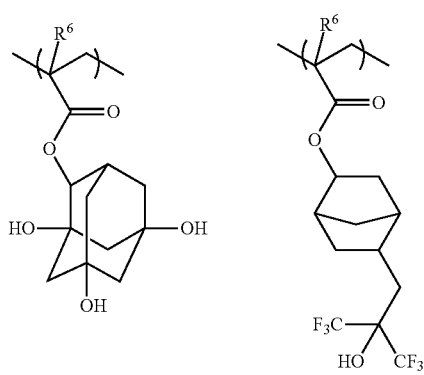

-continued

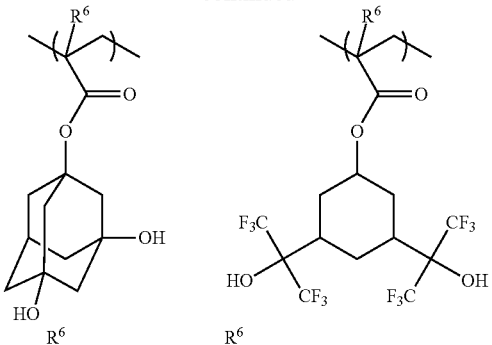
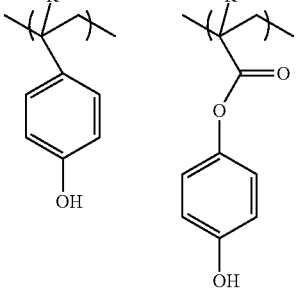

wherein, in the formulae, $R^6$ represents a hydrogen atom, a methyl group or a trifluoromethyl group.

The proportion of the structural unit (IV) in the polymer (A) is preferably 1 mol % to 50 mol %, and more preferably 5 mol % to 30 mol % with respect to entire structural units constituting the polymer (A). In addition, polymer (A) may have one, or two or more types of the structural unit (IV).

In addition to the structural units (I) to (IV), the polymer (A) may include other structural unit. Examples thereof include a structural unit having a cyclic carbonate structure, and the like.

Synthesis Method of Polymer (A)

The polymer (A) may be synthesized according to routine methods such as radical polymerization. The polymer (A) is preferably synthesized, for example, by the following method:

a method in which a reaction solution containing a monomer and a radical initiator is added dropwise to a reaction solution containing a reaction solvent or a monomer, and the mixture is polymerized;

a method in which a reaction solution containing a monomer and a reaction solution containing a radical initiator are each separately added dropwise to another reaction solution containing reaction solvent or a monomer, and the mixture is polymerized;

a method in which one or more reaction solutions each prepared so as to contain each monomer and a reaction solution containing a radical initiator are each separately added dropwise to another reaction solution containing a reaction solvent or a monomer, and the mixture is polymerized; or the like. It should be noted that when the dropwise addition of a monomer solution to another monomer solution is employed to allow the reaction to proceed, the amount of the monomer in the added monomer solution is preferably no less than 30 mol %, more preferably no less than 50 mol %, and particularly preferably 70 mol % with respect to the total amount of the monomer used in the polymerization.

The reaction temperature in these methods may be appropriately determined, depending on the type of the initiator employed. The reaction temperature is typically 30° C. to 180° C., preferably 40° C. to 160° C., and more preferably 50° C. to 140° C. The time required for the dropwise addition may be varied depending on the conditions including the reaction temperature, the type of the initiator, the monomers to be reacted, and the like, but is typically 30 min to 8 hrs, preferably 45 min to 6 hrs, and more preferably 1 hour to 5 hrs. In addition, the total reaction time including the time required for the dropwise addition may be varied depending on the reaction conditions, as is the case with the time required for the dropwise addition, but is typically 30 min to 8 hrs, preferably 45 min to 7 hrs, and more preferably 1 hour to 6 hrs.

Examples of the radical initiator for use in the polymerization include azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile), and the like. These initiators may be used alone or as a mixture of two or more thereof.

The polymerization solvent is not limited as long as the polymerization solvent is not any polymerization-blocking solvent (nitrobenzene, which displays a polymerization-inhibiting effect; mercapto compounds, which displays a chain transferring effect; and the like), and is capable of dissolving the monomers. Examples of the polymerization solvent may include alcohol solvents, ketone solvents, amide solvents, ester or lactone solvents, nitrile solvents, and mixed solvents thereof. These solvents may be used either alone or in combination of two or more types thereof.

The resin obtained in the polymerization reaction is preferably recovered by a reprecipitation method. Specifically, after completion of the polymerization reaction, the targeted resin is recovered as a powder by pouring the polymerization solution into a reprecipitation solvent. Examples of the reprecipitation solvent include alcohols, alkanes and the like, and the alcohols and alkanes may be used alone or as a mixture of two or more thereof. As an alternative to the reprecipitation method, the resin may be recovered by removing low-molecular-weight components such as monomers and oligomers by a liquid separation operation and a column chromatographic operation, an ultrafiltration operation and the like.

The weight average molecular weight (Mw) in terms of the polystyrene equivalent of the polymer (A) as determined by gel permeation chromatography (GPC) is not particularly limited, but is preferably no less than 1,000 and no greater than 100,000, more preferably no less than 2,000 and no greater than 50,000, and particularly preferably no less than 3,000 and no greater than 10,000. The Mw of the polymer (A) of less than 1,000 tends to result in deteriorated heat resistance of the resultant resist. On the other hand, the Mw of the polymer (A) exceeding 500,000 is likely to result in deteriorated developability of the resultant resist.

In addition, the ratio of the Mw to number average molecular weight (Mn) in terms of the polystyrene equivalent as determined by of GPC of polymer (A), i.e., Mw/Mn, is typically no less than 1.0 and no greater than 3, and preferably no less than 1.0 and no greater than 1.5. When the Mw/Mn is within such a range, the resultant resist film tends to have superior resolving performance.

The Mw and Mn used in the present specification refers to those determined by using GPC using columns (manufactured by Tosoh Corporation, G2000HXL×2, G3000HXL×1, G4000HXL×1) under an analytical conditions involving a flow rate of 1.0 mL/min, an elution solvent of tetrahydrofuran, and a column temperature of 40° C., with mono-dispersed polystyrenes as a standard.

Fluorine Atom-Containing Polymer (B)

The radiation-sensitive resin composition may further contain (B) a fluorine atom-containing polymer as a favorable component. When the radiation-sensitive composition contains the polymer (B), the radiation-sensitive composition has enhanced usability for liquid immersion lithography, due to the following positive effects: hydrophobicity of the resist film is improved; superior suppression of the elution of substances is achieved even when liquid immersion lithography is carried out; a sufficiently high receding contact angle between a resist film and a liquid immersion liquid can be achieved; and no water droplet is left during high-speed scanning exposure; and the like.

The form of the fluorine atom-containing polymer (B) may involve, for example:

a structure in which a fluorinated alkyl group is bonded to a main chain;

a structure in which a fluorinated alkyl group is bonded to a side chain; and a structure in which a fluorinated alkyl group is bonded to a main chain and a fluorinated alkyl group is bonded to a side chain.

A monomer that gives the structure in which a fluorinated alkyl group is bonded to a main chain is exemplified by: an α-trifluoromethyl acrylate compound; a β-trifluoromethyl acrylate compound; an α,β-trifluoromethyl acrylate compound; a compound derived by substituting hydrogen(s) of one or more types of vinyl moieties by a fluorinated alkyl group such as a trifluoromethyl group; and the like.

A monomer that gives the structure in which a fluorinated alkyl group is bonded to a side chain is exemplified by: an alicyclic olefin compound such as norbornene having a fluorinated alkyl group and/or a derivative thereof as a side chain; an ester compound of acrylic acid or methacrylic acid having a fluorinated alkyl group and/or a derivative thereof as a side chain; an olefin having a fluorinated alkyl group or a derivative thereof as one or more types of side chain (a site excluding a double bond), and the like.

A monomer that gives the structure in which a fluorinated alkyl group is bonded to a main chain and a fluorinated alkyl group is bonded to a side chain is exemplified by: an ester compound of α-trifluoromethylacrylic acid, β-trifluoromethylacrylic acid, α,β-trifluoromethylacrylic acid, etc., having a fluorinated alkyl group and/or a derivative thereof as a side chain; a compound derived by substituting hydrogen(s) of one or more types of vinyl moieties by a fluorinated alkyl group such as a trifluoromethyl group and substituting a side chain of the compound with a fluorinated alkyl group and/or a derivative thereof; an alicyclic olefin compound derived by substituting hydrogen(s) bonded to one or more types of double bonds by a fluorinated alkyl group such as a trifluoromethyl group and having a fluorinated alkyl group and/or a derivative thereof as a side chain; and the like. It is to be noted that the alicyclic olefin compound as referred to means an alicyclic compound that includes a double bond in a part of its ring.

The polymer (B) preferably has a structural unit (b1) represented by the following formula (6) and/or a structural unit (b2) represented by the formula (7), and may also have "other structural unit" excluding the structural unit (b1) and the structural unit (b2). Each structural unit will be explained in detail below.

Structural Unit (b1)

The structural unit (b1) is represented by the following formula (6):

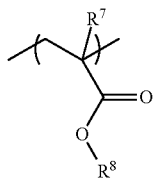

(6)

wherein, in the formula (6), $R^7$ represents a hydrogen atom, a fluorine atom, a methyl group or a trifluoromethyl group; $R^8$ represents a linear or branched alkyl group having 1 to 6 carbon atoms and having a fluorine atom, or a monovalent alicyclic hydrocarbon group having 4 to 20 carbon atoms and having a fluorine atom; wherein a part or all of hydrogen atoms included in the alkyl group and alicyclic hydrocarbon group are not substituted or substituted.

Examples of the linear or branched alkyl group having 1 to 6 carbon atoms include a methyl group, an ethyl group, a propyl group, a butyl group, and the like.

Examples of the monovalent alicyclic hydrocarbon group having 4 to 20 carbon atoms include a cyclopentyl group, a cyclopentylpropyl group, a cyclohexyl group, a cyclohexylmethyl group, a cycloheptyl group, a cyclooctyl group, a cyclooctylmethyl group, and the like.

Examples of the monomer that gives the structural unit (b1) include trifluoromethyl(meth)acrylate, 2,2,2-trifluoroethyl (meth)acrylate, perfluoroethyl(meth)acrylate, perfluoro-n-propyl(meth)acrylate, perfluoro-1-propyl(meth)acrylate, perfluoro-n-butyl(meth)acrylate, perfluoro-1-butyl(meth) acrylate, perfluoro-t-butyl(meth)acrylate, perfluorocyclohexyl(meth)acrylate, 2-(1,1,1,3,3,3-hexafluoro)propyl (meth)acrylate, 1-(2,2,3,3,4,4,5,5-octafluoro)pentyl(meth) acrylate, 1-(2,2,3,3,4,4,5,5-octafluoro)hexyl(meth)acrylate, perfluorocyclohexylmethyl(meth)acrylate, 1-(2,2,3,3,3-pentafluoro)propyl(meth)acrylate, 1-(2,2,3,3,4,4,4-heptafluoro) butyl(meth)acrylate, 1-(3,3,4,4,5,5,6,6,7,7,8,8,9,9,10,10,10-heptadecafluoro)decyl(meth)acrylate, 1-(5-trifluoromethyl-3,3,4,4,5,6,6,6-octafluoro)hexyl(meth)acrylate, and the like.

Examples of the structural unit (b1) include structural unit represented by the following formulae (6-1) and (6-2):

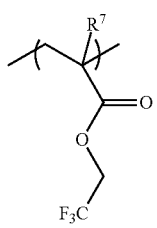

(6-1)

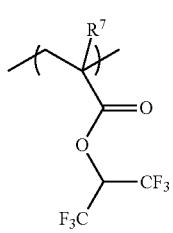

(6-2)

wherein, in the formulae (6-1) and (6-2), $R^7$ is as defined in the above formula (6).

The content of the structural unit (b1) in the polymer (B) is preferably 10 mol % to 70 mol %, and more preferably 20 mol % to 50 mol % with respect to entire structural units constituting the polymer (B). In addition, the polymer (B) may have one, or two or more types of the structural unit (b1).

Structural Unit (b2)

The structural unit (b2) is represented by the following formula (7):

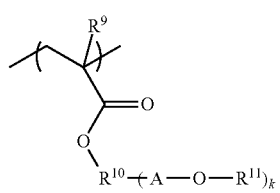

(7)

wherein, in the formula (7), $R^9$ represents a hydrogen atom, a methyl group or a trifluoromethyl group; $R^{10}$ represents a linking group having a valency of (k+1); A represents a divalent linking group having a fluorine atom; $R^{11}$ represents a hydrogen atom or a monovalent organic group; k is an integer of 1 to 3; provided that k is 2 or 3, a plurality of As and a plurality of $R^{11}$s are each the same or different.

In the above formula (7), the linking group having a valency of (k+1) represented by the $R^{10}$ is exemplified by a linear or branched hydrocarbon group having 1 to 30 carbon atoms, an alicyclic hydrocarbon group having 3 to 30 carbon atoms, an aromatic hydrocarbon group having 6 to 30 carbon atoms, or a group derived by combining such a group with at least one selected from the set consisting of an oxygen atom, a sulfur atom, an ether group, an ester group, a carbonyl group, an imino group and an amide group. In addition, the linking group having a valency of (k+1) may have a substituent.

Examples of the linear or branched hydrocarbon group having 1 to 30 carbon atoms include groups derived from any of hydrocarbons such as methane, ethane, propane, butane, pentane, hexane, heptane, decane, icosane and triacontane by removing (k+1) hydrogen atoms therefrom.

Examples of the alicyclic hydrocarbon group having 3 to carbon atoms include groups derived from any of the following hydrocarbons by removing (k+1) hydrogen atoms therefrom:

monocyclic saturated hydrocarbons such as cyclopropane, cyclobutane, cyclopentane, cyclohexane, cycloheptane, cyclooctane, cyclodecane, methylcyclohexane, and ethylcyclohexane;

monocyclic unsaturated hydrocarbons such as cyclobutene, cyclopentene, cyclohexene, cycloheptene, cyclooctene, cyclodecene, cyclopentadiene, cyclohexadiene, cyclooctadiene, and cyclodecadiene;

polycyclic saturated hydrocarbons such as bicyclo[2.2.1] heptane, bicyclo[2.2.2]octane, tricyclo[5.2.1.0$^{2,6}$]decane, tricyclo[3.3.1.1$^{3,7}$]decane, tetracyclo[6.2.1.1$^{3,6}$.0$^{2,7}$]dodecane, and adamantane;

polycyclic hydrocarbons such as bicyclo[2.2.1]heptene, bicyclo[2.2.2]octene, tricyclo[5.2.1.0$^{2,6}$]decene, tricyclo [3.3.1.1$^{3,7}$]decene, and tetracyclo[6.2.1.1$^{3,6}$.0$^{2,7}$]dodecene.

Examples of the aromatic hydrocarbon group having 6 to 30 carbon atoms include groups derived from any of aromatic hydrocarbons such as benzene, naphthalene, phenanthrene, anthracene, tetracene, pentacene, pyrene, picene, toluene, xylene, ethylbenzene, mesitylene and cumene by removing (k+1) hydrogen atoms therefrom.

In the above formula (7), examples of the divalent linking group having a fluorine atom represented by A include divalent linear hydrocarbon groups having 1 to 20 carbon atoms and having a fluorine atom. Examples of the unit A include structures represented by the following formulae (A-1) to (A-6), and the like.

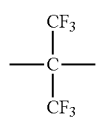
(A-1)

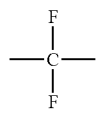
(A-2)

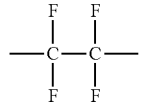
(A-3)

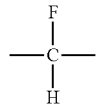
(A-4)

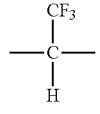
(A-5)

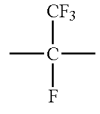
(A-6)

Preferably, the unit A is selected from the structures represented by the above formulae (A-1) and (A-2).

In the above formula (7), examples of the organic group represented by the $R^{11}$ include a linear or branched hydrocarbon group having 1 to 30 carbon atoms, an alicyclic hydrocarbon group having 3 to 30 carbon atoms, an aromatic hydrocarbon group having 6 to 30 carbon atoms, or a group derived by combining such a group with at least one selected from the set consisting of an oxygen atom, a sulfur atom, an ether group, an ester group, a carbonyl group, an imino group and an amide group.

Examples of the structural unit (b2) include structural units represented by the following formulae (7-1) and (7-2):

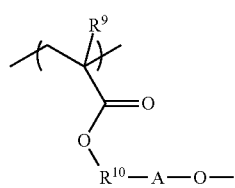
(7-1)

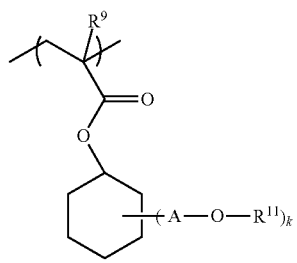
(7-2)

wherein, in the formula (7-1), $R^{10}$ represents a divalent, linear, branched or cyclic, saturated or unsaturated hydrocarbon group having 1 to 20 carbon atoms; $R^9$, A and $R^{11}$ are as defined in the above formula (7); and wherein, in the formula (7-2), $R^9$, A, $R^{11}$ and k are as defined in the above formula (7); wherein k is 2 or 3, a plurality of As and a plurality of $R^{11}$s are each the same or different.

Examples of the structural units represented by the above formula (7-1) and formula (7-2) include structural units represented by the following formula (7-1-1), formula (7-1-2) and formula (7-2-1):

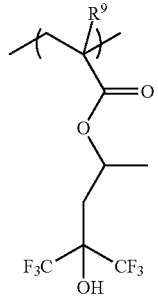
(7-1-1)

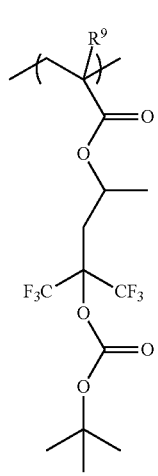
(7-1-2)

-continued

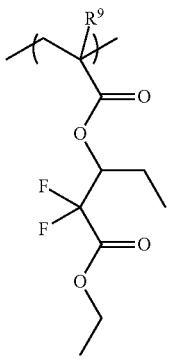
(7-1-3)

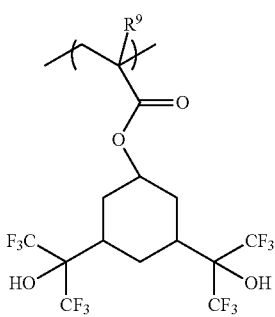
(7-2-1)

wherein, in the formulae (7-1-1), (7-1-2) and (7-2-1), $R^9$ is as defined in the above formula (7).

Examples of the monomer that gives the structural unit (b2) include (meth)acrylic acid (1,1,1-trifluoro-2-trifluoromethyl-2-hydroxy-3-propyl) ester, (meth)acrylic acid (1,1,1-trifluoro-2-trifluoromethyl-2-hydroxy-4-butyl) ester, (meth)acrylic acid (1,1,1-trifluoro-2-trifluoromethyl-2-hydroxy-5-pentyl) ester, (meth)acrylic acid (1,1,1-trifluoro-2-trifluoromethyl-2-hydroxy-4-pentyl) ester, (meth)acrylic acid 2-{[5-(1',1',1'-trifluoro-2'-trifluoromethyl-2'-hydroxy)propyl]bicyclo[2.2.1]heptyl}ester, and the like.

The content of the structural unit (b2) in the polymer (B) is preferably 20 mol % to 80 mol %, and more preferably 30 mol % to 70 mol % with respect to entire structural units constituting the polymer (B). In addition, the polymer (B) may have one, or two or more types of the structural unit (b2).

The content of the other structural unit in the polymer (B) is typically no greater than 90 mol %, preferably 20 mol % to 80 mol %, and more preferably 30 mol % to 70 mol % with respect to entire structural units constituting the polymer (B). In addition, the polymer (B) may have one, or two or more types of the other structural unit.

The blended amount of the polymer (B) is preferably 0.1 parts by mass to 20 parts by mass, more preferably 1 part by mass to 10 parts by mass, and particularly preferably 1 part by mass to 7.5 parts by mass with respect to 100 parts by mass of the polymer (A). When the blended amount of the polymer (B) is less than 0.1 parts by mass, water repellency on the resultant resist surface tends to be insufficient. On the other hand, when the blended amount of the polymer (B) exceeds 20 parts by mass, the water repellency of the resist surface tends to be too high and impaired development is likely to be caused.

The proportion of the fluorine atom in the polymer (B) is preferably higher than that in the polymer (A). The proportion of the fluorine atom in the polymer (B) is typically no less than 5% by mass, preferably 5% by mass to 50% by mass, and more preferably 5% by mass to 45% by mass with respect to the total mass of the polymer (B) (100% by mass). It should be noted that the proportion of the fluorine atom can be determined by $^{13}C$-NMR. When the proportion of the fluorine atom in the polymer (B) is higher than that in the polymer (A), water repellency of a surface of the photoresist film provided by the radiation-sensitive resin composition containing the polymer (B) and polymer (A) tend to be able to be enhanced, and thereby separate preparation of a layer film is no longer required during liquid immersion lithography. In order for the above-mentioned effect to be sufficiently exerted, the difference between the proportion of the fluorine atom in the polymer (B) and the proportion of the fluorine atom in the polymer (A) is preferably no less than 1% by mass, and more preferably no less than 5% by mass.

Synthesis Method of Polymer (B)

The polymer (B) may be prepared, for example, by polymerizing a monomers corresponding to each certain structural unit in an appropriate solvent using a radical polymerization initiator.

Examples of solvents for use in the polymerization include:

alkanes such as n-pentane, n-hexane, n-heptane, n-octane, n-nonane, and n-decane;

cycloalkanes such as cyclohexane, cycloheptane, cyclooctane, decalin, and norbornane;

aromatic hydrocarbons such as benzene, toluene, xylene, ethylbenzene, and cumene;

halogenated hydrocarbons such as chlorobutanes, bromohexanes, dichloroethanes, hexamethylene dibromide, and chlorobenzene;

saturated carboxylate esters such as ethyl acetate, n-butyl acetate, i-butyl acetate, and methyl propionate;

ketones such as acetone, 2-butanone, 4-methyl-2-pentanone, and 2-heptanone;

ethers such as tetrahydrofuran, dimethoxyethanes, and diethoxyethanes;

alcohols such as methanol, ethanol, 1-propanol, 2-propanol, and 4-methyl-2-pentanol; and the like. These solvents may be used alone, or in combination of two or more thereof.

The reaction temperature in the polymerization is typically 40° C. to 150° C., and preferably 50° C. to 120° C. The reaction time is typically 1 hour to 48 hrs, and preferably 1 hour to 24 hrs.

Mw of the polymer (B) is preferably 1,000 to 50,000, more preferably 2,000 to 20,000, and particularly preferably 2,500 to 10,000. The Mw of the polymer (B) is less than 1,000, a sufficient receding contact angle tends to be hardly achieved. On the other hand, the Mw exceeding 50,000 is likely to result in deteriorated developability of the resultant resist.

In the polymer (B), the ratio of the Mw to its number average molecular weight (Mn) in terms of the polystyrene equivalent as determined by a GPC method, i.e., Mw/Mn, is preferably 1 to 5, and more preferably 1 to 4.

<Acid Generator (C)>

The acid generator (C) generates an acid upon the exposure, and dissociates an acid-dissociable group present in the polymer (A) by means of the acid, rendering the polymer (A) soluble in a developer solution. The mode of incorporation of the acid generator (C) into the composition may be a form of being incorporated as a compound as described below (hereinafter, may be referred to as "acid generating agent (C)", as appropriately), a form of being incorporated as a part of a polymer, or a mixture thereof.

Examples of the acid generating agent (C) include onium salt compounds, sulfonimide compounds, halogen-containing compounds, diazoketone compounds, and the like. Among the acid generating agents (C), the onium salt compounds are preferred.

Examples of the onium salt compounds include sulfonium salts (including tetrahydrothiophenium salts), iodonium salts, phosphonium salts, diazonium salts, pyridinium salts, and the like.

Examples of the sulfonium salts include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, triphenylsulfonium camphorsulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-cyclohexylphenyldiphenylsulfonium camphorsulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, 4-methanesulfonylphenyldiphenylsulfonium camphorsulfonate, triphenylphosphonium 1,1,2,2-tetrafluoro-6-(1-adamantanecarbonyloxy)-hexane-1-sulfonate, triphenylsulfonium 1,1-difluoro-2-adamantane-ethane-1-sulfonate, and the like. Among these, triphenylsulfonium trifluoromethanesulfonate, triphenylsulfonium nonafluoro-n-butanesulfonate, triphenylphosphonium 1,1,2,2-tetrafluoro-6-(1-adamantanecarbonyloxy)-hexane-1-sulfonate, and triphenylsulfonium 1,1-difluoro-2-adamantane-ethane-1-sulfonate are preferred.

Examples of the tetrahydrothiophenium salts include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl) tetrahydrothiophenium 2-bicyclo[2.2.1]hept-2-yl-1,1,2,2-tetrafluoroethanesulfonate, 1-(4-n-butoxynaphthalen-1-yl) tetrahydrothiophenium camphorsulfonate, 1-(6-n-butoxynaphthalen-2-yl)tetrahydrothiophenium trifluoromethanesulfonate, 1-(6-n-butoxynaphthalen-2-yl) tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl) tetrahydrothiophenium 2-bicyclo[2.2.1]hept-2-yl-1,1,2,2-tetrafluoroethanesulfonate, 1-(6-n-butoxynaphthalen-2-yl) tetrahydrothiophenium camphorsulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium camphorsulfonate, and the like. Among these tetrahydrothiophenium salts, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate and 1-(3,5-dimethyl-4-hydroxyphenyl)tetrahydrothiophenium nonafluoro-n-butanesulfonate are preferred.

Examples of the iodonium salts include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, diphenyliodonium camphorsulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, bis(4-t-butylphenyl)iodonium camphorsulfonate, and the like. Among these iodonium salts, bis(4-t-butylphenyl)iodonium nonafluoro-n-butanesulfonate is preferred.

Examples of the sulfonimide compounds may include N-(trifluoromethanesulfonyloxy)bicyclo[2.2.1]hept-5-ene-2,3-dicarboxylmide, N-(nonafluoro-n-butanesulfonyloxy) bicyclo[2.2.1]hept-5-ene-2,3-dicarboxylmide, N-(perfluoro-n-octanesulfonyloxy)bicyclo[2.2.1]hept-5-ene-2,3-dicarboxylmide, N-(2-bicyclo[2.2.1]hept-2-yl-1,1,2,2-tetrafluoroethanesulfonyloxy)bicyclo[2.2.1]hept-5-ene-2,3-dicarboxylmide, N-(2-(3-tetracyclo[4.4.0.1$^{2,5}$.1$^{7,10}$] dodecanyl)-1,1-difluoroethanesulfonyloxy)bicyclo[2.2.1] hept-5-ene-2,3-dicarboxylmide, N-(camphorsulfonyloxy) bicyclo[2.2.1]hept-5-ene-2,3-dicarboxylmide, and the like. Among these sulfonimide compounds, N-(trifluoromethanesulfonyloxy)bicyclo[2.2.1]hept-5-ene-2,3-dicarboxylmide is preferred.

These acid generating agents (C) may be used alone, or in combination of two or more thereof. The amount of the acid generator (C) employed in the case of the acid generator (C) being the acid generating agent is typically no less than 0.1 parts by mass and no greater than 25 parts by mass, preferably no less than 5 parts by mass and no greater than 20 parts by mass with respect to 100 parts by mass of the polymer (A) in view of ensuring the sensitivity and developability for use as a resist. In this case, when the amount of the acid generating agent (C) employed is less than 0.1 parts by mass, the sensitivity and developability tend to be deteriorated, whereas the amount of the acid generating agent (C) exceeding 25 parts by mass is likely to result in reduction of radiation transmittance, and to render the formation of the desired resist patterns difficult.

Acid Diffusion Controller (D)

The acid diffusion controller exerts the effect of controlling diffusion phenomenon of the acid generated from the acid generator (C) upon the exposure in the resist coating film, and suppressing unfavorable chemical reactions in unexposed regions; as a result, storage stability of the resultant radiation-sensitive resin composition is further improved, and resolution of the resist is further improved, while suppressing variation of line width of the resist pattern caused by variation of post-exposure delay (PED) from the exposure to development treatment, which enables the radiation-sensitive resin composition with superior process stability to be obtained. The mode of incorporation of acid diffusion controller into the composition may be a form of being incorporation as a free compound as described below (hereinafter, may be also referred to as "acid diffusion control agent (D)"), a form of being incorporation as a part of a polymer, or a mixture thereof.

Examples of the acid diffusion control agent include amine compounds, amide group-containing compounds, urea compounds, nitrogen-containing heterocyclic compounds, and the like.

Examples of the amine compounds include mono(cyclo) alkylamines; di(cyclo)alkylamines; tri(cyclo)alkylamines; substituted alkylaniline or derivatives thereof; ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis(1-(4-aminophenyl)-1-methylethyl)benzene, 1,3-bis(1-(4-aminophenyl)-1-methylethyl)benzene, bis(2-dimethylaminoethyl)ether, bis(2-diethylaminoethyl)ether, 1-(2-hydroxyethyl)-2-imidazolidinone, 2-quinoxalinol, N,N,N',N'-tetrakis(2-hydroxypropyl)ethylenediamine, N,N,N',N''N''-pentamethyldiethylenetriamine, and the like.

Examples of the amide group-containing compounds include N-t-butoxycarbonyl group-containing amino compounds, formamide, N-methylformamide, N,N-dimethylformamide, acetamide, N-methylacetamide, N,N-dimethylacetamide, propionamide, benzamide, pyrrolidone, N-methylpyrrolidone, N-acetyl-1-adamantylamine, tris(2-hydroxyethyl) isocyanurate, and the like.

Examples of the urea compounds include urea, methylurea, 1,1-dimethylurea, 1,3-dimethylurea, 1,1,3,3-tetramethylurea, 1,3-diphenylurea, tri-n-butylthiourea, and the like.

Examples of the nitrogen-containing heterocyclic compounds include imidazoles; pyridines; piperazines; pyrazine, pyrazole, pyridazine, quinoxaline, purine, pyrrolidine, piperidine, piperidine ethanol, 3-piperidino-1,2-propanediol, morpholine, 4-methylmorpholine, 1-(4-morpholinyl)ethanol, 4-acetylmorpholine, 3-(N-morpholino)-1,2-propanediol, 1,4-dimethylpiperazine, 1,4-diazabicyclo[2.2.2]octane, N-t-amyloxycarbonyl-4-hydroxypiperidine, and the like.

In addition, the acid diffusion control agent may be a photodegradable base which is sensitized upon exposure to generate a weak acid. An example of the photodegradable base includes onium salt compounds which degrade upon the exposure and lose their acid diffusion controllability. Examples of the onium salt compounds include sulfonium salt compounds represented by the following formula (8), and iodonium salt compounds represented by the following formula (9):

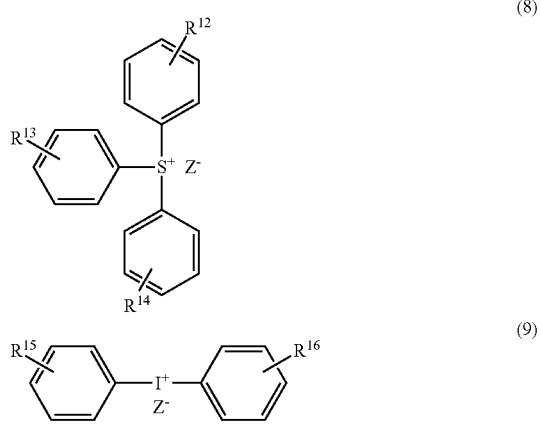

wherein, in the formula (8) and the formula (9), $R^{12}$ to $R^{16}$ represents each independently a hydrogen atom, an alkyl group, an alkoxyl group, a hydroxyl group or a halogen atom; and wherein, in the formula (8) and the formula (9), $Z^-$ represents $OH^-$, $R^{17}-COO^-$ or $R^{17}-SO_3^-$, wherein $R^{17}$ represents an alkyl group, an aryl group, an alkaryl group or an anion represented by the following formula (10):

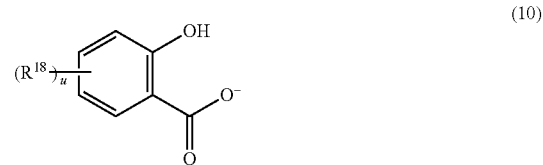

wherein, in the formula (10), $R^{18}$ represents a linear or branched alkyl group having 1 to 12 carbon atoms, or a linear or branched alkoxyl group having 1 to 12 carbon atoms, wherein a part or all of hydrogen atoms included in the above alkyl group and alkoxyl group are not substituted or substituted by a fluorine atom; and u is 1 or 2.

These acid diffusion controllers may be used alone, or in combination of two or more thereof. The content of the acid diffusion control agent is preferably less than 10 parts by mass with respect to 100 parts by mass of the polymer (A). When the total amount of the acid diffusion control agent used exceeds 5 parts by mass, the sensitivity for use as a resist tends to be deteriorated.

Solvent (E)

The composition typically contains a solvent. The solvent is not particularly limited as long as the solvent can at least dissolve the polymer (A), the polymer (B), the acid generator (C), the acid diffusion controller (D), and optional components added as required. Examples of the solvent include alcohol solvents, ether solvents, ketone solvents, amide solvents, ester solvents and mixed solvents thereof, and the like.

Examples of the alcohol solvents include:

monoalcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol, and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, and tripropylene glycol;

polyhydric alcohol partial ether solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether; and the like.

Examples of the ketone solvents include acetone, methyl ethyl ketone, methyl n-propyl ketone, methyl n-butyl ketone, diethyl ketone, methyl iso-butyl ketone, methyl n-pentyl ketone, ethyl n-butyl ketone, methyl n-hexyl ketone, di-isobutyl ketone, trimethylnonanone, cyclopentanone, cyclohexanone, cycloheptanone, cyclooctanone, methylcyclohexanone, 2,4-pentanedione, acetonylacetone, diacetone alcohol, acetophenone, and the like.

Examples of the amide solvents include N,N'-dimethyl imidazolidinone, N-methylformamide, N,N-dimethylformamide, N,N-diethylformamide, acetamide, N-methylacetamide, N,N-dimethylacetamide, N-methylpropionamide, N-methylpyrrolidone, and the like.

Examples of the ester solvents include diethyl carbonate, propylene carbonate, methyl acetate, ethyl acetate, γ-butyrolactone, γ-valerolactone, n-propyl acetate, iso-propyl acetate, n-butyl acetate, iso-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxytriglycol acetate, ethyl propionate, n-butyl propionate, iso-amyl propionate, diethyl oxalate, di-n-butyl oxalate, methyl lactate, ethyl lactate, n-butyl lactate, n-amyl lactate, diethyl malonate, dimethyl phthalate, diethyl phthalate, and the like.

Examples of the other solvents include:

aliphatic hydrocarbon solvents such as n-pentane, iso-pentane, n-hexane, iso-hexane, n-heptane, iso-heptane, 2,2,4-trimethylpentane, n-octane, iso-octane, cyclohexane, and methylcyclohexane;

aromatic hydrocarbon solvents such as benzene, toluene, xylene, mesitylene, ethylbenzene, trimethylbenzene, methylethylbenzene, n-propylbenzene, iso-propylbenzene, diethylbenzene, iso-butylbenzene, triethylbenzene, di-iso-propylbenzene, and n-amylnaphthalene;

halogen-containing solvents such as dichloromethane, chloroform, flons, chlorobenzene, and dichlorobenzene; and the like.

Among the solvents, propylene glycol monomethyl ether acetate, cyclohexanone, and γ-butyrolactone are preferred.

Other Optional Components

In addition to the polymer (A), an essential component, as well as the polymer (B), the acid generator (C), the acid diffusion control agent (D), and the solvent (E), which are added as required, the radiation-sensitive resin composition may contain a surfactant, an alicyclic skeleton-containing compound, a sensitizing agent and the like as other optional components, within a range not leading to impairment of the effects of the present invention.

Surfactant

The surfactant exerts the effect of improving coating property, striation, developability and the like.

Alicyclic Skeleton-Containing Compound

The alicyclic skeleton-containing compound exerts the effect of improving dry-etching resistance, pattern configuration, adhesiveness to a substrate, and the like.

Sensitizing Agent

The sensitizing agent exhibits the action of increasing the amount of the acid generator (C) produced, and exerts the effect of improving "apparent sensitivity" of the composition.

Preparation of Radiation-Sensitive Resin Composition

The composition may be prepared by mixing the polymer (A), the polymer (B), the acid generator (C), the acid diffusion control agent (D), the solvent (E), and the other optional components in a predetermined ratio. In addition, the composition may be prepared and used in the state of being dissolved or dispersed in an appropriate organic solvent.

Pattern-Forming Method

The pattern-forming method according to an embodiment of the present invention includes the steps of:

(1) coating the radiation-sensitive resin composition onto a substrate to provide a resist film (hereinafter, may be also referred to as step (1)), (2) exposing the resist film (hereinafter, may be also referred to as step (2)), (3) heating the exposed resist film at a temperature of no greater than 110° C. (hereinafter, may be also referred to as step (3)), and (4) developing the heated resist film (hereinafter, may be also referred to as step (4)).

Hereinafter, each step will be explained in detail.

Step (1)

In this step, a resist film is provided by coating the radiation-sensitive resin composition or a composition solution obtained by dissolving the same in a solvent, onto a substrate such as a silicon wafer, silicon dioxide, a wafer covered with an antireflective film by coating techniques such as spin-coating, cast coating, roll coating, so as to achieve a predetermined film thickness, and subsequently evaporating the solvent present in the coated film through prebaking.

Step (2)

In this step, the resist film provided in the step (1) is exposed by irradiating the same with radioactive rays (in some cases, through a liquid immersion medium such as water). It should be noted that, during the exposure, the resist film is irradiated with the radioactive rays through a mask having a predetermined pattern. The radioactive ray employed is appropriately selected from visible light rays, ultraviolet rays, far ultraviolet rays, X-rays, charged particle rays and the like in accordance with the line width of the targeted pattern. Far ultraviolet rays typified by ArF excimer laser (wavelength: 193 nm) and KrF excimer laser (wavelength: 248 nm) are preferably used, and an ArF excimer laser is more preferable.

Step (3)

Subsequently, the exposed photoresist film is subjected to post exposure baking (PEB), and thereby the polymer at the exposed sites of the resist film is deprotected by the acid generated from the acid generating agent (C). In the embodiment of the present invention, the PEB is carried out at temperatures appropriately selected within a temperature range of no greater than 110° C. In the pattern-forming method of the embodiment of the present invention, since the temperature of the PEB may be set to no greater than 110° C., energy consumption in the manufacturing process thereof may be saved.

It should be noted that the temperature for the PEB is preferably no less than 60° C. and no greater than 110° C., and more preferably no less than 70° C. and no greater than 110° C. The temperatures for the PEB of no less than 80° C. and no greater than 110° C. are particularly preferred. At the temperature below 60° C., sufficient deprotection tends to be hardly achieved.

Step (4)

In this step, the exposed resist film is developed with a developer solution to form the predetermined photoresist pattern. After the development, washing with water and drying are typically carried out. The developer solution is preferably an aqueous alkali solution prepared by dissolving at least one of alkaline compounds such as, for example, sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo[5.4.0]-7-undecene, 1,5-diazabicyclo [4.3.0]-5-nonene in water.

In addition, when liquid immersion lithography is carried out, a protective film for liquid immersion, which is insoluble in a liquid used in the liquid immersion, may be provided on a resist film before the step (2), in order to protect the resist film from direct contact with the liquid used in immersion liquid. A solvent-removal type protective film which is stripped with a solvent before the step (4) (see, for example, Japanese Unexamined Patent Application, Publication No. 2006-227632), and a developer-soluble type protective film which is stripped simultaneously with the development (see, for example, WO2005-069076, and WO2006-035790) may be used as the protective film for liquid immersion. However, use of the developer-soluble type protective film for liquid immersion is preferred in view of throughput.

The resist pattern thus obtained exhibits superior resolving ability, and is suitable for microfabrication utilizing lithography techniques.

EXAMPLES

Hereinafter, the present invention will be explained more specifically by way of Examples, but the present invention is not limited to these Examples. It should be noted that "parts" and "%" used in Examples and Comparative Examples are on mass basis, unless otherwise indicated. Measuring methods of each physical properties and evaluation methods for various properties are described in the following.

Mw and Mn of polymers were determined by using GPC columns (Tosoh Corporation, G2000HXL×2, G3000HXL×1, G4000HXL×1) under the following analytical condition:
column temperature: 40° C.
elution solvent: tetrahydrofuran (Wako Pure Chemical Industries, Ltd.)
flow rate: 1.0 mL/min
sample concentration: 1.0% by mass
sample injection amount: 100 μL
detector: differential refractometer
standard substance: mono-dispersed polystyrene $^{13}$C-NMR analysis was carried out using a nuclear magnetic resonance apparatus (JEOL, Ltd., JNM-EX270).

The residual ratio (%) of low-molecular-weight components was determined by high performance liquid chromatography (HPLC) using a column manufactured and sold by GL Sciences, Inc. under the trade name "Inertsil ODS-25 μm column" (4.6 mm σ×250 mm) under an analytical condition involving a flow rate of 1.0 mL/min, elution solvent of acrylonitrile/0.1% aqueous phosphoric acid solution. Used herein, the term "low-molecular-weight components" means any component having a molecular weight of less than 1,000.

Synthesis of Polymer (A)

Synthesis Example 1

A monomer solution was prepared by dissolving 37.56 g (40 mol %) of the compound (M-3), 6.28 g (5 mol %) of the compound (M-5), 6.22 g (10 mol %) of the compound (M-8), 12.74 g (10 mol %) of the compound (M-9), and 37.21 g (35 mol %) of the compound (M-11) in 200 g of 2-butanone, and adding 7.85 g of AIBN thereto. A 1,000 mL three-neck flask containing 100 g of 2-butanone was purged with nitrogen for 30 min, and heated to 80° C. with stirring, and thereafter the monomer solution prepared above was added dropwise thereto via a dropping funnel over 3 hrs. The time of the start of the dropwise addition was considered to be the time of the initiation of the polymerization reaction, and the polymerization reaction was allowed to proceed for 6 hrs. After completion of the polymerization reaction, the polymerization solution was cooled to no greater than 30° C. via water-cooling. The cooled polymerization solution was poured into 2,000 g of methanol, and a white powder deposited was filtered off. The filtered white powder was washed twice with 400 g of methanol, filtered, and dried at 50° C. for 17 hrs to obtain the polymer (A-1) as a white powder (70 g; yield: 70%). The polymer (A-1) thus obtained had an Mw of 4,300, an Mw/Mn of 1.37, and a residual ratio of the low-molecular-weight components of 0.05%. In addition, the polymer (A-1) was a copolymer having proportions of the structural unit derived from the compound (M-3):the structural unit derived from the compound (M-5):the structural unit derived from the compound (M-8):the structural unit derived from the compound (M-9):the structural unit derived from the compound (M-11) of 38.6:4.2:11.0:10.8:45.4 (mol %).

Synthesis Examples 2 to 21

The polymers (A-2) to (A-15) and (a-1) to (a-6) were obtained in a similar manner to Synthesis Example 1 except that the monomers specified in Tables 1-1 and 1-2 were blended in the predetermined amount. In addition, Tables 1-1 and 1-2 collectively present the Mw, Mw/Mn, and yield (%) of the respective polymers obtained, and the content of the structural units derived from the respective monomers in the respective polymers. It should be noted that the monomers used in the synthesis of the polymer (A), and the monomers used in synthesis of the polymer (B) described below are represented by the following formulae.

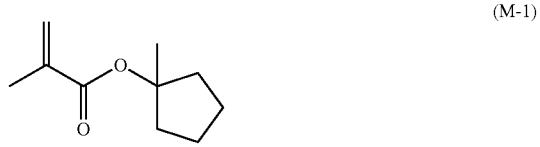

(M-1)

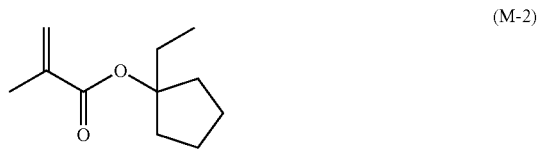

(M-2)

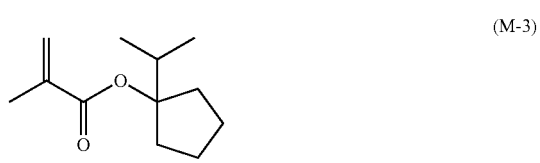

(M-3)

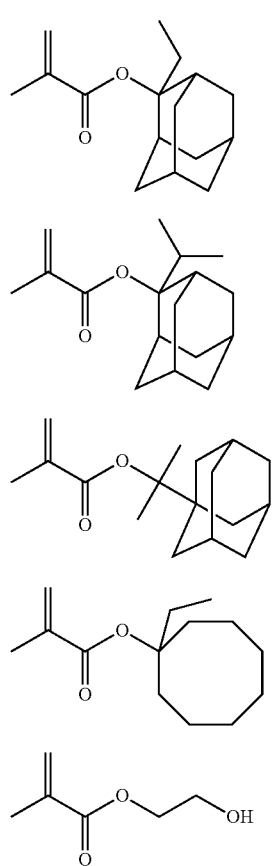

(M-4)
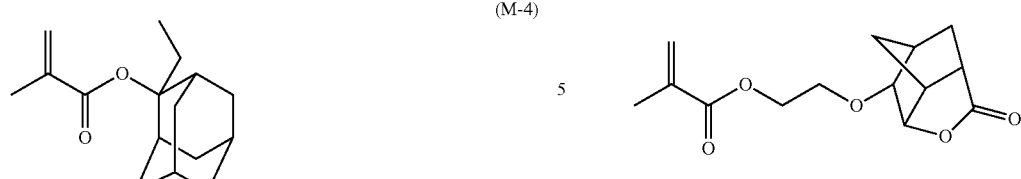

(M-5)
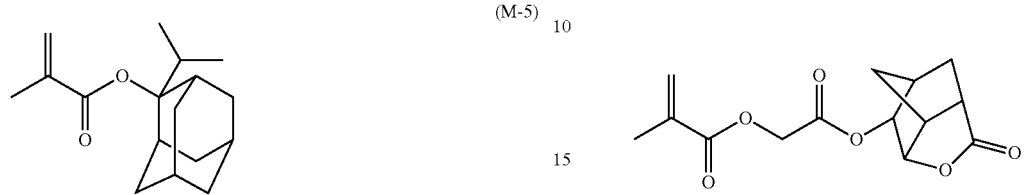

(M-6)
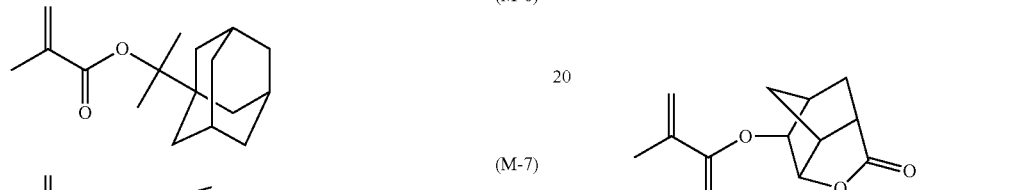

(M-7)
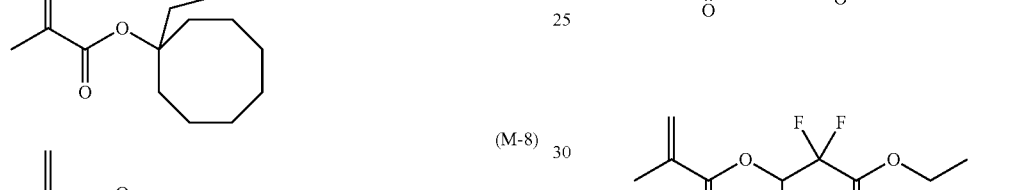

(M-8)

(M-9)

(M-10)
(M-11)
(M-12)
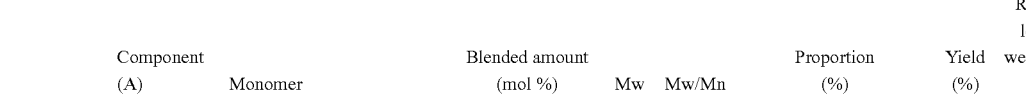

TABLE 1-1

| | Component (A) | Monomer | Blended amount (mol %) | Mw | Mw/Mn | Proportion (%) | Yield (%) | Residual ratio of low-molecular-weight components (%) |
|---|---|---|---|---|---|---|---|---|
| Synthesis Example 1 | (A-1) | (M-3)/(M-5)/(M-8)/(M-9)/(M-11) | 40/05/10/10/35 | 4,300 | 1.37 | 38.6/4.2/11.0/10.8/45.4 | 70 | 0.05 |
| Synthesis Example 2 | (A-2) | (M-3)/(M-5)/(M-6)/(M-9)/(M-11) | 40/05/10/45 | 4,100 | 1.3 | 39.0/5.0/10.3/45.7 | 68 | 0.05 |
| Synthesis Example 3 | (A-3) | (M-2)/(M-4)/(M-9)/(M-11) | 40/10/10/40 | 4,300 | 1.4 | 39.0/8.7/11.3/46.0 | 71 | 0.03 |
| Synthesis Example 4 | (A-4) | (M-3)/(M-5)/(M-8)/(M-10)/(M-11) | 40/05/10/10/35 | 4,250 | 1.38 | 38.7/4.1/11.1/10.9/45.4 | 65 | 0.05 |
| Synthesis Example 5 | (A-5) | (M-3)/(M-5)/(M-10)/(M-11) | 40/05/10/45 | 4,150 | 1.31 | 39.1/4.9/10.4/45.6 | 69 | 0.05 |
| Synthesis Example 6 | (A-6) | (M-2)/(M-4)/(M-10)/(M-11) | 40/10/10/40 | 4,200 | 1.3 | 39.2/8.5/11.3/46.0 | 71 | 0.03 |
| Synthesis Example 7 | (A-7) | (M-1)/(M-4)/(M-10)/(M-11) | 30/10/20/40 | 4,500 | 1.36 | 39.5/9.5/20.7/45.3 | 72 | 0.05 |
| Synthesis Example 8 | (A-8) | (M-1)/(M-6)/(M-10)/(M-11) | 30/10/20/40 | 4,450 | 1.3 | 39.6/9.4/20.8/45.2 | 70 | 0.05 |
| Synthesis Example 9 | (A-9) | (M-1)/(M-10)/(M-11) | 30/10/60 | 4,600 | 1.45 | 31.0/9.8/59.2 | 66 | 0.04 |
| Synthesis Example 10 | (A-10) | (M-4)/(M-10)/(M-11) | 30/20/50 | 4,200 | 1.4 | 30.5/20.2/49.3 | 67 | 0.05 |
| Synthesis Example 11 | (A-11) | (M-2)/(M-6)/(M-9)/(M-11) | 15/35/20/30 | 4,100 | 1.3 | 15.1/34.9/20.3/29.7 | 72 | 0.05 |

TABLE 1-2

| | Component (A) | Monomer | Blended amount (mol %) | Mw | Mw/Mn | Proportion (%) | Yield (%) | Residual ratio of low-molecular-weight components (%) |
|---|---|---|---|---|---|---|---|---|
| Synthesis Example 12 | (A-12) | (M-2)/(M-6)/(M-10)/(M-11) | 15/35/20/30 | 4,150 | 1.35 | 15.2/34.9/20.2/29.7 | 70 | 0.09 |
| Synthesis Example 13 | (A-13) | (M-2)/(M-6)/(M-10)/(M-11) | 35/15/20/30 | 4,100 | 1.3 | 35.2/14.9/20.2/29.7 | 70 | 0.09 |
| Synthesis Example 14 | (A-14) | (M-3)/(M-4)/(M-10)/(M-11) | 15/35/30/20 | 4,300 | 1.35 | 15.2/34.9/30.2/19.7 | 70 | 0.05 |
| Synthesis Example 15 | (A-15) | (M-1)/(M-6)/(M-10)/(M-11) | 30/10/20/40 | 4,500 | 1.7 | 39.8/9.2/20.6/45.4 | 75 | 0.05 |
| Synthesis Example 16 | (a-1) | (M-3)/(M-5)/(M-8)/(M-11) | 40/05/10/45 | 4,100 | 1.35 | 38.5/4.0/10.5/46.0 | 77 | 0.05 |
| Synthesis Example 17 | (a-2) | (M-3)/(M-5)/(M-11) | 40/10/50 | 4,200 | 1.4 | 39.0/9.4/51.6 | 78 | 0.05 |
| Synthesis Example 18 | (a-3) | (M-2)/(M-4)/(M-8)/(M-11) | 35/10/10/45 | 4,150 | 1.41 | 35.4/9.5/10.0/45.1 | 80 | 0.06 |
| Synthesis Example 19 | (a-4) | (M-1)/(M-6)/(M-11) | 40/10/50 | 4,200 | 1.3 | 40.7/9.3/50.0 | 76 | 0.05 |
| Synthesis Example 20 | (a-5) | (M-2)/(M-6)/(M-11) | 15/35/50 | 4,300 | 1.43 | 15.5/34.4/50.1 | 75 | 0.05 |
| Synthesis Example 21 | (a-6) | (M-2)/(M-4)/(M-9) | 30/20/50 | 4,250 | 1.3 | 31.5/20.5/48 | 75 | 0.05 |

Synthesis of Polymer (B)

Synthesis Example 21

A monomer solution was prepared by dissolving 37.41 g (40 mol %) of the compound (M-7) and 62.59 g (60 mol %) of the compound (M-12) in 100 g of 2-butanone, and adding 4.79 g of AIBN thereto. A 1000 mL three-neck flask containing 100 g of 2-butanone was purged with nitrogen for 30 min, and heated to 80° C. with stirring, and thereafter the monomer solution prepared above was added dropwise thereto via a dropping funnel over 3 hrs. The time of the start of the dropwise addition was considered to be the time of the initiation of the polymerization reaction, and the polymerization reaction was allowed to proceed for 6 hrs. After completion of the polymerization reaction, the polymerization solution was cooled to no greater than 30° C. via water-cooling. The polymerization solution was concentrated under vacuum on an evaporator until the weight of the polymerization solution was reduced to 150 g. Thereafter, the concentrated solution was poured into a mixed liquid of 760 g of methanol and 40 g of water to deposit a slimy white solid. The liquid portion was removed by decantation, and the recovered solid was dried under vacuum at 60° C. for 15 hrs to obtain 47 g of the polymer (B-1) as a white powder (yield 47%). The polymer (B-1) had an Mw of 3,700, and an Mw/Mn of 1.40. In addition, the result of $^{13}$C-NMR analysis revealed that the polymer (B-1) was a copolymer having proportions of the repeating unit derived form the compound (M-7):the repeating unit derived form the compound (M-12) of 42.5:57.5 (mol %). It should be noted that the chemical formulae of the monomers employed are shown below.

Preparation of Radiation-Sensitive Resin Composition

The acid generating agent (C), the acid diffusion controller (D) and the solvent (E) used in the preparation of the composition are as follows:

Acid Generating Agent (C)

C-1: triphenylsulfonium 1,1,2,2-tetrafluoro-6-(1-adamantanecarbonyloxy)-hexane-1-sulfonate C-2: triphenylsulfonium 1,1-difluoro-2-adamantane-ethane-1-sulfonate

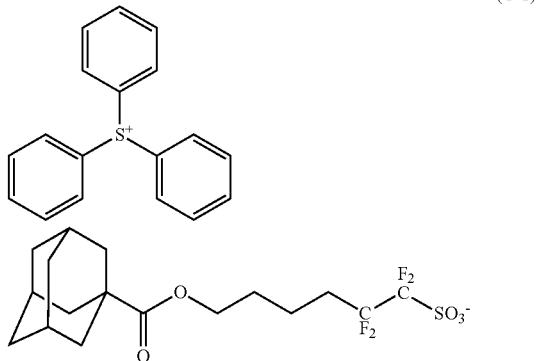

(C-1)

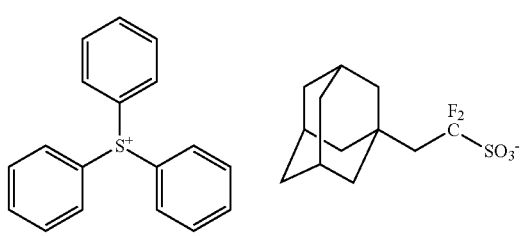

(C-2)

Acid Diffusion Control Agent (D)

D-1: triphenylsulfonium salicylate (the compound represented by the following formula (D-1))

D-2: N-t-amyloxycarbonyl-4-hydroxypiperidine (the compound represented by the following formula (D-2))

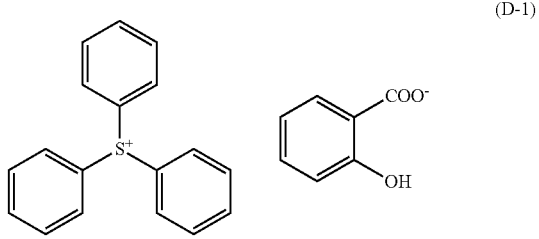

(D-1)

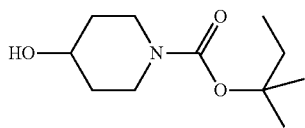

(D-2)

Solvent (E)

In the following, the solvents used in Examples and Comparative Examples are described.
E-1: propylene glycol monomethyl ether acetate
E-2: cyclohexanone
E-3: γ-butyrolactone

Example 1

A radiation-sensitive resin composition was prepared by mixing 100 parts by mass of the polymer (A-1) obtained in Synthesis Example 1, 3 parts by mass of the polymer (B-1) obtained in Synthesis Example 19, 11 parts by mass of the acid generating agent (C-1), 7.9 parts by mass of the acid diffusion control agent (D-1), and 2,590 parts by mass of the solvent (E-1), 1,110 parts by mass of the solvent (E-2), 200 parts by mass of the solvent (E-3), and filtering the mixed solution thus obtained through a filter with a pore size of 0.20 μm. The radiation-sensitive resin composition was designated as composition (J-1).

Examples 2 to 16, Comparative Examples 1 to 5

The compositions (J-2) to (J-16) and (j-1) to (j-5) for use in the respective radiation-sensitive resin compositions were prepared in a similar manner to Example 1 except that the blend formulations specified in Tables 2-1 to 2-4 were employed.

TABLE 2-1

| | Radiation-sensitive resin composition | Component (A) Type | Amount used (parts by mass) | Component (B) Type | Amount used (parts by mass) | Acid generating agent (C) Type | Amount used (parts by mass) | Acid diffusion controller (D) Type | Amount used (parts by mass) | Solvent (E) Type | Amount used (parts by mass) |
|---|---|---|---|---|---|---|---|---|---|---|---|
| Example 1 | (J-1) | (A-1) | 100 | (B-1) | 3 | (C-1) | 11 | (D-1) | 7.9 | (E-1) | 2590 |
| | | | | | | | | | | (E-2) | 1110 |
| | | | | | | | | | | (E-3) | 200 |
| Example 2 | (J-2) | (A-2) | 100 | (B-1) | 3 | (C-1) | 11 | (D-1) | 7.9 | (E-1) | 2590 |
| | | | | | | | | | | (E-2) | 1110 |
| | | | | | | | | | | (E-3) | 200 |
| Example 3 | (J-3) | (A-3) | 100 | (B-1) | 3 | (C-1) | 11 | (D-1) | 7.9 | (E-1) | 2590 |
| | | | | | | | | | | (E-2) | 1110 |
| | | | | | | | | | | (E-3) | 200 |
| Example 4 | (J-4) | (A-4) | 100 | (B-1) | 3 | (C-1) | 11 | (D-1) | 7.9 | (E-1) | 2590 |
| | | | | | | | | | | (E-2) | 1110 |
| | | | | | | | | | | (E-3) | 200 |
| Example 5 | (J-5) | (A-5) | 100 | (B-1) | 3 | (C-1) | 11 | (D-1) | 7.9 | (E-1) | 2590 |
| | | | | | | | | | | (E-2) | 1110 |
| | | | | | | | | | | (E-3) | 200 |
| Example 6 | (J-6) | (A-6) | 100 | (B-1) | 3 | (C-1) | 11 | (D-1) | 7.9 | (E-1) | 2590 |
| | | | | | | | | | | (E-2) | 1110 |
| | | | | | | | | | | (E-3) | 200 |

TABLE 2-2

| | Radiation-sensitive resin composition | Component (A) Type | Amount used (parts by mass) | Component (B) Type | Amount used (parts by mass) | Acid generating agent (C) Type | Amount used (parts by mass) | Acid diffusion controller (D) Type | Amount used (parts by mass) | Solvent (E) Type | Amount used (parts by mass) |
|---|---|---|---|---|---|---|---|---|---|---|---|
| Example 7 | (J-7) | (A-7) | 100 | (B-1) | 3 | (C-1) | 8 | (D-1) | 1.5 | (E-1) | 2205 |
| | | | | | | (C-2) | 5 | | | (E-2) | 945 |
| | | | | | | | | | | (E-3) | 150 |
| Example 8 | (J-8) | (A-8) | 100 | (B-1) | 3 | (C-1) | 8 | (D-1) | 1.5 | (E-1) | 2205 |
| | | | | | | (C-2) | 5 | | | (E-2) | 945 |
| | | | | | | | | | | (E-3) | 150 |
| Example 9 | (J-9) | (A-9) | 100 | (B-1) | 3 | (C-1) | 8 | (D-1) | 1.5 | (E-1) | 2205 |
| | | | | | | (C-2) | 5 | | | (E-2) | 945 |
| | | | | | | | | | | (E-3) | 150 |

TABLE 2-3

| Radiation-sensitive resin composition | Component (A) Type | Amount used (parts by mass) | Component (B) Type | Amount used (parts by mass) | Acid generating agent (C) Type | Amount used (parts by mass) | Acid diffusion controller (D) Type | Amount used (parts by mass) | Solvent (E) Type | Amount used (parts by mass) |
|---|---|---|---|---|---|---|---|---|---|---|
| Example 10 (J-10) | (A-10) | 100 | (B-1) | 3 | (C-1) | 8 | (D-1) | 1.5 | (E-1) | 2205 |
| | | | | | (C-2) | 5 | | | (E-2) | 945 |
| | | | | | | | | | (E-3) | 150 |
| Example 11 (J-11) | (a-3) | 50 | (B-1) | 3 | (C-1) | 11 | (D-1) | 7.9 | (E-1) | 2590 |
| | (a-6) | 50 | | | | | | | (E-2) | 1110 |
| | | | | | | | | | (E-3) | 200 |
| Example 12 (J-12) | (A-11) | 100 | (B-1) | 3 | (C-1) | 8.4 | (D-1) | 2.5 | (E-1) | 1780 |
| | | | | | | | | | (E-2) | 760 |
| | | | | | | | | | (E-3) | 200 |
| Example 13 (J-13) | (A-12) | 100 | (B-1) | 3 | (C-1) | 8.4 | (D-1) | 2.5 | (E-1) | 1780 |
| | | | | | | | | | (E-2) | 760 |
| | | | | | | | | | (E-3) | 200 |
| Example 14 (J-14) | (A-13) | 100 | (B-1) | 3 | (C-1) | 8.4 | (D-1) | 2.5 | (E-1) | 1780 |
| | | | | | | | | | (E-2) | 760 |
| | | | | | | | | | (E-3) | 200 |

TABLE 2-4

| Radiation-sensitive resin composition | Component (A) Type | Amount used (parts by mass) | Component (B) Type | Amount used (parts by mass) | Acid generating agent (C) Type | Amount used (parts by mass) | Acid diffusion controller (D) Type | Amount used (parts by mass) | Solvent (E) Type | Amount used (parts by mass) |
|---|---|---|---|---|---|---|---|---|---|---|
| Example 15 (J-15) | (A-14) | 100 | (B-1) | 3 | (C-1) | 8.4 | (D-1) | 2.5 | (E-1) | 2205 |
| | | | | | | | | | (E-2) | 945 |
| | | | | | | | | | (E-3) | 150 |
| Example 16 (J-16) | (A-15) | 100 | (B-1) | 3 | (C-1) | 8 | (D-1) | 1.5 | (E-1) | 1780 |
| | | | | | (C-2) | 5 | | | (E-2) | 760 |
| | | | | | | | | | (E-3) | 200 |
| Comparative Example 1 (j-1) | (a-1) | 100 | (B-1) | 3 | (C-1) | 11 | (D-1) | 7.9 | (E-1) | 2590 |
| | | | | | | | | | (E-2) | 1110 |
| Comparative Example 2 (j-2) | (a-2) | 100 | (B-1) | 3 | (C-1) | 11 | (D-1) | 7.9 | (E-1) | 2590 |
| | | | | | | | | | (E-2) | 1110 |
| | | | | | | | | | (E-3) | 200 |
| Comparative Example 3 (j-3) | (a-3) | 100 | (B-1) | 3 | (C-1) | 11 | (D-1) | 7.9 | (E-1) | 2590 |
| | | | | | | | | | (E-2) | 1110 |
| | | | | | | | | | (E-3) | 200 |
| Comparative Example 4 (j-4) | (a-4) | 100 | (B-1) | 3 | (C-1) | 8.4 | (D-1) | 2.5 | (E-1) | 1780 |
| | | | | | | | | | (E-2) | 760 |
| | | | | | | | | | (E-3) | 200 |
| Comparative Example 5 (j-5) | (a-5) | 100 | (B-1) | 3 | (C-1) | 8.4 | (D-1) | 2.5 | (E-1) | 1780 |

Evaluation of LS (Line & Spaces) Pattern

The radiation-sensitive resin compositions obtained in Examples 1 to 11 and 16, and Comparative Examples 1 to 4 were evaluated for LWR, MEEF and trench DOF using an ArF excimer laser as a light source, in accordance with the evaluation method described below (Examples 17 to 30 and Comparative Examples 6 to 10). It should be noted that the conditions for the SB and PEB conducted on the respective radiation-sensitive resin compositions are shown in Tables 3-1 to 3-3.

Line Width Roughness (LWR)

First, the radiation-sensitive resin composition was used to provide a coating film of a film thickness of 75 nm on a 12-inch silicon wafer having an underlayer antireflective film ("ARC66", manufactured by Nissan Chemical Industries, Ltd.) provided thereon, and the coating film was subjected to soft baking (SB) at the temperatures specified in Tables 3-1 to 3-3 for 60 sec. Subsequently, the coating film was exposed using an ArF excimer laser Immersion Scanner ("NSR S610C", manufactured by NIKON Corporation) through a mask pattern for forming a pattern having a line of 50 nm and a pitch of 100 nm, under the conditions involving NA of 1.3, a ratio of 0.800, and Annular. After the exposure, the respective radiation-sensitive resin compositions were subjected to post-baking (PEB) at the temperatures specified in Tables 3-1 to 3-3 for 60 sec. Thereafter, the radiation-sensitive resin composition was developed with a 2.38% by mass aqueous tetramethylammonium hydroxide solution, followed by rinsing with water, and drying to form a positive type resist pattern. In this process, an exposure dose ($J/m^2$) resulting in formation of lines having a line width of 50 nm in the sites exposed through the mask pattern for forming the pattern having a line of 50 nm and a pitch of 100 nm was designated as optimum exposure dose (Eop). It should be noted that a scanning electron microscope ("CG-4000", manufactured by Hitachi High-Technologies Corporation) was used in the line-width measurement.

In the observation of the lines having a line width of 50 nm formed with the Eop as defined above, line widths at arbitrary ten points were measured when observed from above the pattern, and 3 Sigma (degree of distribution) of measurements of the line widths was defined as "LWR (nm)". When the LWR value is no greater than 5 nm, the formed pattern configuration was determined to be favorable.

Mask Error Factor (MEEF)

LS patterns having a pitch of 100 nm were formed with the Eop as defined above through any of masks which gave patterns of 48 nm lines with a pitch of 100 nm, 49 nm lines with a pitch of 100 nm, 50 nm lines with a pitch of 100 nm, 51 nm lines with a pitch of 100 nm, or 52 nm lines with a pitch of 100 nm. In this process, the line width (nm) formed on the resist film with each mask pattern (ordinate) was plotted against the line size (nm) of the designed pattern size of each mask (abscissa) to obtain a straight line, and a slope of the straight line was calculated as MEEF. When MEEF (the slope of the straight line) is no greater than 4, mask reproducibility was determined to be favorable.

Depth of Focus (DOF) for Trench Pattern

A mask to form a pattern having a trench width of 50 nm and a pitch of 160 nm was prepared. Each resist composition was irradiated through the mask with the Eop defined above several times with changing the focal point along the optical axis of the irradiation. "DOF (nm) for trench" means the maximum distance of the focal points where a pattern having a trench width between 45 nm and 55 nm was obtained. The DOF for trench of no less than 70 nm was determined to be favorable.

The evaluation results are shown in Tables 3-1 to 3-3.

TABLE 3-1

| | Radiation-sensitive resin composition | SB | | PEB | | Evaluation result | | | |
|---|---|---|---|---|---|---|---|---|---|
| | | Temperature (° C.) | Time (sec) | Temperature (° C.) | Time (sec) | Eop (J/m$^2$) | LWR (nm) | MEEF | DOF for trench (nm) |
| Example 17 | (J-1) | 120 | 60 | 80 | 60 | 39 | 5 | 3.7 | 90 |
| Example 18 | (J-2) | 120 | 60 | 80 | 60 | 35 | 5 | 3.8 | 80 |
| Example 19 | (J-3) | 120 | 60 | 80 | 60 | 40 | 5 | 3.6 | 90 |
| Example 20 | (J-4) | 120 | 60 | 80 | 60 | 39 | 4.5 | 3.6 | 80 |
| Example 21 | (J-5) | 120 | 60 | 80 | 60 | 36 | 4.8 | 3.7 | 70 |
| Example 22 | (J-6) | 120 | 60 | 80 | 60 | 40 | 4.9 | 3.5 | 80 |
| Example 23 | (J-7) | 100 | 60 | 95 | 60 | 30 | 4.8 | 3.5 | 80 |

TABLE 3-2

| | Radiation-sensitive resin composition | SB | | PEB | | Evaluation result | | | |
|---|---|---|---|---|---|---|---|---|---|
| | | Temperature (° C.) | Time (sec) | Temperature (° C.) | Time (sec) | Eop (J/m$^2$) | LWR (nm) | MEEF | DOF for trench (nm) |
| Example 24 | (J-8) | 100 | 60 | 95 | 60 | 33 | 4.9 | 3.3 | 80 |
| Example 25 | (J-8) | 100 | 60 | 100 | 60 | 31 | 4.8 | 3.4 | 70 |
| Example 26 | (J-8) | 100 | 60 | 105 | 60 | 29 | 5 | 3.7 | 70 |
| Example 27 | (J-9) | 100 | 60 | 100 | 60 | 31 | 4.5 | 3.4 | 90 |
| Example 28 | (J-10) | 100 | 60 | 90 | 60 | 30 | 5 | 3.5 | 80 |
| Example 29 | (J-11) | 120 | 60 | 80 | 60 | 34 | 4.9 | 3.6 | 80 |
| Example 30 | (J-16) | 100 | 60 | 95 | 60 | 30 | 5 | 3.9 | 70 |

TABLE 3-3

| | Radiation-sensitive resin composition | SB | | PEB | | Evaluation result | | | |
|---|---|---|---|---|---|---|---|---|---|
| | | Temperature (° C.) | Time (sec) | Temperature (° C.) | Time (sec) | Eop (J/m$^2$) | LWR (nm) | MEEF | DOF for trench (nm) |
| Comparative Example 6 | (j-1) | 120 | 60 | 80 | 60 | 37 | 5.4 | 3.7 | 50 |
| Comparative Example 7 | (j-2) | 120 | 60 | 80 | 60 | 37 | 5.4 | 3.7 | 50 |
| Comparative Example 8 | (j-3) | 120 | 60 | 80 | 60 | 41 | 5.6 | 3.5 | 60 |
| Comparative Example 9 | (j-4) | 120 | 60 | 105 | 60 | 35 | 5.6 | 3.6 | 60 |
| Comparative Example 10 | (j-8) | 100 | 60 | 115 | 60 | 28 | 5.2 | 4.1 | 60 |

As shown in Tables 3-1 to 3-3, the use of the radiation-sensitive resin composition allowed for the improvement of LWR and DOF, while keeping superior MEEF in the LS (line & spaces pattern).

Evaluation of Contact Hole Pattern

The radiation-sensitive resin compositions obtained in Examples 12 to 15 and Comparative Example 5 were evaluated for CDU and MEEF using an ArF excimer laser as a light source in accordance with the evaluation method described below (Examples 31 to 34 and Comparative Example 11).

Critical Dimension Uniformity (CDU)

First, the radiation-sensitive resin composition was used to provide a coating film of a film thickness of 100 nm on a 12-inch silicon wafer having an underlayer antireflective film ("ARC66", manufactured by Nissan Chemical Industries, Ltd.) provided thereon, and the coating film was subjected to soft baking (SB) at 100° C. for 60 sec. Thereafter, the coating film was exposed through a mask pattern for forming a pattern of 75 nm holes with a pitch of 110 nm, using an ArF excimer laser Immersion Scanner ("NSR S610C", manufactured by NIKON Corporation) under the conditions involving NA of 1.3, a ratio of 0.800, and Annular. After the exposure, each radiation-sensitive resin composition was subjected to post-baking (PEB) at the temperature specified in Tables 3-1 to 3-3 for 60 sec. Thereafter, the radiation-sensitive resin composition was developed with a 2.38% by mass aqueous tetramethylammonium hydroxide solution, followed by rinsing with water, and drying to form a positive type resist pattern. In this process, an exposure dose forming a hole having a diameter of 65 nm in the portions exposed through a mask pattern of 75 nm holes with a pitch of 110 nm was designated as optimum exposure dose (Eop). It should be noted that a scanning electron microscope ("CG-4000", manufactured by Hitachi High-Technologies Corporation) was used in the line-width measurement. A total of 30 hole patterns having a diameter of 65 nm formed with the Eop defined above were subjected to line-width measurement, an average deviation of the measurement values obtained in the line-width measurement of the total of 30 hole patterns was calculated, and CDU was calculated by trebling the average deviation. The CDU of no greater than 4 was determined to be favorable.

Mask Error Factor (MEEF)

The diameter (nm) of the hole formed in the resist film with the Eop as defined above using portions of a mask pattern having a hole diameter (as a designed pattern size) of 73 nm, 74 nm, 75 nm, 76 nm, and 77 nm (ordinate) was plotted against the size (nm) of the mask pattern (abscissa) to obtain a straight line, and a slope of the straight line was calculated as MEEF. The MEEF of no greater than 5.0 was determined to be favorable.

Depth of Focus (DOF) for Hole Pattern

Each resist composition was irradiated through the mask with the Eop defined above several times with changing the focal point along the optical axis of the irradiation. "DOF (nm) for hole" means the maximum distance of the focal points where a pattern having a hole diameter between 60 nm and 70 nm was obtained. The DOF for hole of no less than 100 nm was determined to be favorable.

The evaluation results are shown in Table 4.

TABLE 4

| | Radiation-sensitive resin composition | SB Temperature (° C.) | SB Time (sec) | PEB Temperature (° C.) | PEB Time (sec) | Evaluation result Eop (J/m$^2$) | Evaluation result CDU (nm) | Evaluation result MEEF | Evaluation result DOF for hole (nm) |
|---|---|---|---|---|---|---|---|---|---|
| Example 31 | (J-12) | 100 | 60 | 90 | 60 | 50.5 | 3.7 | 4.5 | 120 |
| Example 32 | (J-13) | 100 | 60 | 90 | 60 | 52.5 | 3.5 | 4.6 | 120 |
| Example 33 | (J-14) | 100 | 60 | 95 | 60 | 50 | 3.7 | 4.5 | 120 |
| Example 34 | (J-15) | 100 | 60 | 85 | 60 | 48 | 3.5 | 4.6 | 120 |
| Comparative Example 11 | (j-5) | 100 | 60 | 90 | 60 | 54.5 | 4.3 | 4.7 | 80 |

As shown in Table 4, the use of the radiation-sensitive resin composition allowed for further improvement of the CDU and DOF, while maintaining superior MEEF values in the contact hole pattern.

According to the embodiment of the present invention, there can be provided a radiation-sensitive resin composition which exhibits improved LWR, CDU and DOF and superior lithography properties while sufficiently maintaining not only basic properties such as sensitivity, but also high MEEF property, as well as a method for forming a resist pattern from the radiation-sensitive resin composition.

Obviously, numerous modifications and variations of the present invention are possible in light of the above teachings. It is therefore to be understood that within the scope of the appended claims, the invention may be practiced otherwise than as specifically described herein.

What is claimed is:

1. A radiation-sensitive resin composition for forming a resist film, comprising:

a polymer comprising at least one polymer molecule, the at least one polymer molecule comprising:

a first structural unit represented by formula (1); and a second structural unit represented by formula (2);

a third structural unit comprising an acid-dissociable group and being represented by formula (4); and a fourth structural unit other than the third structural unit, comprising an acid-dissociable group and being represented by the formula (4), the first structural unit, the second structural unit, the third structural unit and the fourth structural unit being included in an identical polymer molecule or different polymer molecules,

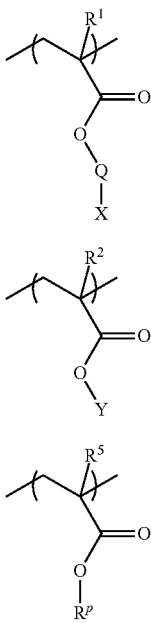

(1)

(2)

(4)

wherein, in the formula (1), $R^1$ represents a hydrogen atom or a methyl group; Q represents —$R^3$—$R^4$—O—*, wherein $R^3$ represents an alkylene group having 1 to 3 carbon atoms, $R^4$ represents a single bond or a carbonyl group, and * indicates a bonding site to X; X represents a monovalent lactone group optionally substituted with a linear or branched alkyl group having 1 to 4 carbon atoms, a linear or branched alkoxy group having 1 to 4 carbon atoms, in the formula (2), $R^2$ represents a hydrogen atom or a methyl group; Y represents a monovalent lactone group optionally substituted with a linear or branched alkyl group having 1 to 4 carbon atoms, a linear or branched alkoxy group having 1 to 4 carbon atoms, a cyano group, —$CF_3$, —$COOCH_3$, or —$OCH_3$, and in the formula (4), $R^5$ represents a hydrogen atom, a methyl group or a trifluoromethyl group; and $R^p$ represents an acid-dissociable group, the radiation-sensitive resin composition being for use in a pattern-forming method, comprising:
providing the resist film on a substrate;
exposing the resist film;
heating the exposed resist film at a temperature of no greater than 110° C.; and
developing the heated resist film.

2. The radiation-sensitive resin composition according to claim 1, wherein the lactone groups represented by X and Y are not substituted.

3. The radiation-sensitive resin composition according to claim 1, wherein the Q represents —$CH_2CH_2O$—* or —$CH_2COO$—*, wherein * indicates a bonding site to X.

4. The radiation-sensitive resin composition according to claim 1, wherein each of the lactone groups X and Y are the identical.

5. The radiation-sensitive resin composition according to claim 1, wherein each of the lactone groups represented by X and Y has a norbornane lactone skeleton.

6. The radiation-sensitive resin composition according to claim 1, wherein an Mw/Mn of the polymer is no less than 1.0 and no greater than 1.5.

7. A pattern-forming method, comprising:
coating the radiation-sensitive resin composition according to claim 1 on a substrate to provide a resist film;
exposing the resist film;
heating the exposed resist film at a temperature of no greater than 110° C.; and
developing the heated resist film.

8. The radiation-sensitive resin composition according to claim 1, wherein $R^p$ in the formula (4) is represented by formula (5):

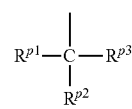

(5)

wherein, in the formula (5), $R^{p1}$ represents an alkyl group having 1 to 4 carbon atoms or a monovalent alicyclic hydrocarbon group having 4 to 20 carbon atoms; $R^{p2}$ and $R^{p3}$ each represent an alkyl group having 1 to 4 carbon atoms or an alicyclic hydrocarbon group having 4 to 20 carbon atoms, or $R^{p2}$ and $R^{p3}$ taken together represent a divalent alicyclic hydrocarbon group having 4 to 20 carbon atoms.

9. The radiation-sensitive resin composition according to claim 8, wherein $R^{p2}$ and $R^{p3}$ taken together represent a divalent alicyclic hydrocarbon group comprising an adamantane skeleton or a cycloalkane skeleton.

10. The radiation-sensitive resin composition according to claim 1, wherein the first structural unit and the second structural unit are included in the identical polymer molecule.

11. The radiation-sensitive resin composition according to claim 1, wherein the first structural unit and the second structural unit are included in different polymer molecules.

12. The radiation-sensitive resin composition according to claim 1, wherein the monovalent lactone group represented by Y is unsubstituted or substituted with a linear or branched alkyl group having 1 to 4 carbon atoms, a linear or branched alkoxy group having 1 to 4 carbon atoms, —$CF_3$, —$COOCH_3$, or —$OCH_3$.

* * * * *